(12) United States Patent
Fallows et al.

(10) Patent No.: US 12,702,586 B2
(45) Date of Patent: Aug. 11, 2026

(54) PAD DESIGNS TO IMPROVE DELIVERY OF TEMPERATURE THERAPY

(71) Applicant: C. R. Bard, Inc., Franklin Lakes, NJ (US)

(72) Inventors: Eric A. Fallows, Apex, NC (US); Nicholas J. Jardine, Holly Springs, NC (US); Qihua Xu, Cary, NC (US); Adam T. Martin, Holly Springs, NC (US); Sean E. Walker, Platteville, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 256 days.

(21) Appl. No.: 18/272,026

(22) PCT Filed: Jan. 11, 2022

(86) PCT No.: PCT/US2022/011980
§ 371 (c)(1),
(2) Date: Jul. 12, 2023

(87) PCT Pub. No.: WO2022/155132
PCT Pub. Date: Jul. 21, 2022

(65) Prior Publication Data

US 2024/0065884 A1 Feb. 29, 2024

Related U.S. Application Data

(60) Provisional application No. 63/136,335, filed on Jan. 12, 2021.

(51) Int. Cl.
*A61F 7/02* (2006.01)
*A61F 7/00* (2006.01)

(52) U.S. Cl.
CPC .............. *A61F 7/02* (2013.01); *A61F 7/0085* (2013.01); *A61F 2007/0054* (2013.01)

(58) Field of Classification Search
CPC ...... A61F 2007/0018; A61F 2007/0054; A61F 2007/0056; A61F 7/00; A61F 7/0085;
(Continued)

(56) References Cited

U.S. PATENT DOCUMENTS 2,167,865 A 8/1939 Beecher
2,250,325 A 7/1941 Barnes
(Continued)

FOREIGN PATENT DOCUMENTS

AU 678753 B3 6/1997
AU 2007201161 B2 12/2010
(Continued)

OTHER PUBLICATIONS

PCT/US2021/065144 filed Dec. 23, 2021 International Search Report dated Oct. 4, 2022.
(Continued)

*Primary Examiner* — Michael F Peffley
(74) *Attorney, Agent, or Firm* — Rutan & Tucker LLP

(57) ABSTRACT

Disclosed herein are systems and methods for providing targeted temperature management (TTM) therapy to a patient. The TTM system can include multiple embodiments of a thermal pad including embodiments that are convertible from a first patient contact area to a second patient contact area. Embodiments of thermal pads can include pads that are expandable, extendable, and/or comprise attachable or removable portions. The TTM system can include embodiments where a second thermal pad is coupled to a first thermal pad.

22 Claims, 13 Drawing Sheets

(58) Field of Classification Search
CPC .... A61F 7/02; A61F 7/08; A61F 7/086; A61F 7/10; A61F 7/103
See application file for complete search history.

(56) References Cited

U.S. PATENT DOCUMENTS 2,296,207 A 9/1942 Joyce
2,595,328 A 5/1952 Bowen
2,602,302 A 7/1952 Poux
2,726,658 A 12/1955 Chessey
2,807,809 A 10/1957 Kottemann
3,075,529 A 1/1963 Young, Jr.
3,091,242 A 5/1963 Johnson et al.
3,212,286 A 10/1965 Curtis
3,506,013 A 4/1970 Zdenek
3,734,293 A 5/1973 Biskis
3,830,676 A 8/1974 Elkins
3,867,939 A 2/1975 Moore et al.
3,900,035 A 8/1975 Welch et al.
3,927,671 A 12/1975 Chittenden et al.
3,945,617 A 3/1976 Callery
3,995,621 A 12/1976 Fletcher et al.
4,059,293 A 11/1977 Sipler
4,092,982 A 6/1978 Salem
4,108,146 A 8/1978 Golden
4,114,620 A 9/1978 Moore et al.
4,118,946 A 10/1978 Tubin
4,149,541 A 4/1979 Gammons et al.
4,154,245 A 5/1979 Daily
4,161,210 A 7/1979 Reid et al.
4,195,631 A 4/1980 Baucom
4,311,022 A 1/1982 Hall
4,444,727 A 4/1984 Yanagihara et al.
4,508,123 A 4/1985 Wyatt et al.
4,580,408 A 4/1986 Stuebner
4,753,241 A 6/1988 Brannigan et al.
4,834,705 A 5/1989 Vaillancourt
4,846,176 A 7/1989 Golden
4,867,748 A 9/1989 Samuelsen
4,884,304 A 12/1989 Elkins
4,886,063 A 12/1989 Crews
4,908,248 A 3/1990 Nakashima et al.
4,919,134 A 4/1990 Streeter
4,962,761 A 10/1990 Golden
4,971,056 A 11/1990 Seacord
4,981,135 A 1/1991 Hardy
4,989,607 A 2/1991 Keusch et al.
5,000,252 A 3/1991 Faghri
5,005,374 A 4/1991 Spitler
5,050,596 A 9/1991 Walasek et al.
5,062,414 A 11/1991 Grim
5,072,875 A 12/1991 Zacoi
5,090,409 A 2/1992 Genis
5,097,829 A 3/1992 Quisenberry
5,111,668 A 5/1992 Parrish et al.
5,113,666 A 5/1992 Parrish et al.
5,133,348 A 7/1992 Mayn
5,146,625 A 9/1992 Steele et al.
5,154,706 A 10/1992 Cartmell et al.
5,190,032 A 3/1993 Zacoi
5,265,669 A 11/1993 Schneider
5,268,022 A 12/1993 Garrett et al.
5,289,695 A 3/1994 Parrish et al.
5,300,103 A 4/1994 Stempel et al.
5,304,213 A 4/1994 Berke et al.
5,304,216 A 4/1994 Wallace
5,320,164 A 6/1994 Szczesuil et al.
5,329,638 A 7/1994 Hansen et al.
5,383,919 A 1/1995 Kelly et al.
5,393,462 A 2/1995 Avery
5,405,366 A 4/1995 Fox et al.
5,407,421 A 4/1995 Goldsmith
5,409,500 A 4/1995 Dyrek
5,411,541 A 5/1995 Bell et al.
5,423,751 A 6/1995 Harrison et al.
5,431,622 A 7/1995 Pyrozyk et al.
5,437,673 A 8/1995 Baust et al.
5,456,701 A 10/1995 Stout
5,466,250 A 11/1995 Johnson, Jr. et al.
5,470,353 A 11/1995 Jensen
5,476,489 A 12/1995 Koewler
5,484,448 A 1/1996 Steele et al.
5,486,207 A 1/1996 Mahawili
5,514,169 A 5/1996 Dickerhoff et al.
5,545,194 A 8/1996 Augustine
5,566,413 A 10/1996 Webb et al.
5,605,144 A 2/1997 Simmons et al.
5,609,620 A 3/1997 Daily
5,620,482 A 4/1997 Augustine et al.
5,624,477 A 4/1997 Armond
5,634,940 A 6/1997 Panyard
5,640,728 A 6/1997 Graebe
5,645,855 A 7/1997 Lorenz
5,658,325 A 8/1997 Augustine
5,662,695 A 9/1997 Mason et al.
5,683,439 A 11/1997 Jensen
5,720,774 A 2/1998 Glucksman
5,733,318 A 3/1998 Augustine
5,755,755 A 5/1998 Panyard
5,785,716 A 7/1998 Bayron et al.
5,806,335 A 9/1998 Herbert et al.
5,824,025 A 10/1998 Augustine
5,837,002 A 11/1998 Augustine et al.
5,840,080 A 11/1998 Der Ovanesian
5,843,145 A 12/1998 Brink
5,871,526 A 2/1999 Gibbs et al.
5,879,378 A 3/1999 Usui
5,887,437 A 3/1999 Maxim
5,913,849 A 6/1999 Sundstrom et al.
5,948,012 A 9/1999 Mahaffey et al.
5,968,000 A 10/1999 Harrison et al.
5,986,163 A 11/1999 Augustine
5,989,285 A 11/1999 DeVilbiss et al.
6,010,528 A 1/2000 Augustine et al.
6,019,783 A 2/2000 Philips et al.
6,030,412 A 2/2000 Klatz et al.
6,047,106 A 4/2000 Salyer
6,074,415 A 6/2000 Der Ovanesian
6,083,256 A 7/2000 Der Ovanesian
6,083,418 A 7/2000 Czarnecki et al.
6,117,164 A 9/2000 Gildersleeve et al.
6,176,869 B1 1/2001 Mason et al.
6,176,870 B1 1/2001 Augustine
6,185,744 B1 2/2001 Poholski
6,188,930 B1 2/2001 Carson
6,189,149 B1 2/2001 Allen
6,189,550 B1 2/2001 Stickel et al.
6,197,045 B1 3/2001 Carson
6,234,538 B1 5/2001 Lauer
6,238,427 B1 5/2001 Matta
6,255,552 B1 7/2001 Cummings et al.
6,257,011 B1 7/2001 Siman-Tov et al.
6,290,716 B1 9/2001 Augustine
6,336,935 B1 1/2002 Davis et al.
6,349,560 B1 2/2002 Maier-Laxhuber et al.
6,352,550 B1 3/2002 Gildersleeve et al.
6,364,937 B1 4/2002 McMahon
6,371,976 B1 * 4/2002 Vrzalik ................ A61F 7/0097 607/104
6,375,674 B1 4/2002 Carson
6,389,839 B1 5/2002 Sabin
6,436,130 B1 8/2002 Philips et al.
6,451,036 B1 9/2002 Heitzmann et al.
6,454,792 B1 9/2002 Noda et al.
6,461,379 B1 10/2002 Carson et al.
6,463,212 B1 10/2002 Salyer
6,503,297 B1 1/2003 Lu et al.
6,508,831 B1 1/2003 Kushnir
6,508,859 B1 1/2003 Zia et al.
6,511,501 B1 1/2003 Augustine et al.
6,511,502 B2 1/2003 Fletcher
6,517,510 B1 2/2003 Stewart et al.
D471,987 S 3/2003 Hoglund et al.
D472,322 S 3/2003 Hoglund et al.

(56) References Cited

U.S. PATENT DOCUMENTS 6,551,348 B1 4/2003 Blalock et al.
D474,544 S 5/2003 Hoglund et al.
6,559,096 B1 5/2003 Smith et al.
6,584,797 B1 7/2003 Smith et al.
6,589,270 B2 7/2003 Augustine
6,591,630 B2 7/2003 Smith et al.
6,601,404 B1 8/2003 Roderick
6,613,030 B1 9/2003 Coles et al.
6,620,187 B2 9/2003 Carson et al.
6,620,188 B1 9/2003 Ginsburg et al.
6,645,232 B2 11/2003 Carson
6,648,905 B2 11/2003 Hoglund et al.
6,653,607 B2 11/2003 Ellis et al.
D483,125 S 12/2003 Hoglund et al.
6,660,027 B2 12/2003 Gruszecki et al.
6,669,715 B2 12/2003 Hoglund et al.
6,682,525 B2 1/2004 Lalonde et al.
D487,147 S 2/2004 Ellingboe et al.
D487,148 S 2/2004 Ellingboe et al.
6,688,132 B2 2/2004 Smith et al.
6,692,518 B2 2/2004 Carson
6,699,267 B2 3/2004 Voorhees et al.
6,701,724 B2 3/2004 Smith et al.
6,743,250 B2 6/2004 Renfro
6,755,801 B2 6/2004 Utterberg et al.
6,755,852 B2 6/2004 Lachenbruch et al.
D492,773 S 7/2004 Ellingboe et al.
6,770,848 B2 8/2004 Haas et al.
6,799,063 B2 9/2004 Carson
6,800,087 B2 10/2004 Papay et al.
6,802,855 B2 10/2004 Ellingboe et al.
6,802,885 B2 10/2004 Luk et al.
6,818,012 B2 11/2004 Ellingboe
6,827,728 B2 12/2004 Ellingboe et al.
6,846,322 B2 1/2005 Kane et al.
6,858,068 B2 2/2005 Smith et al.
6,878,156 B1 4/2005 Noda
6,893,453 B2 5/2005 Agarwal et al.
6,904,956 B2 6/2005 Noel
6,909,074 B1 6/2005 Bradley
6,921,198 B2 7/2005 Gruszecki et al.
6,931,875 B1 8/2005 Allen et al.
6,942,644 B2 9/2005 Worthen
6,960,243 B1 11/2005 Smith et al.
6,968,711 B2 11/2005 Smith et al.
6,969,399 B2 11/2005 Schock et al.
7,008,445 B2 3/2006 Lennox
7,022,099 B2 4/2006 Litzie et al.
7,044,960 B2 5/2006 Voorhees et al.
7,052,509 B2 5/2006 Lennox et al.
7,055,575 B2 6/2006 Noel
7,056,335 B2 6/2006 Agarwal et al.
7,063,718 B2 6/2006 Dobak, III
7,077,858 B2 7/2006 Fletcher et al.
7,097,657 B2 8/2006 Noda et al.
7,101,389 B1 9/2006 Augustine et al.
7,122,047 B2 10/2006 Grahn et al.
7,160,316 B2 1/2007 Hamilton et al.
7,172,586 B1 2/2007 Dae et al.
7,240,720 B2 7/2007 Noel
7,303,554 B2 12/2007 Lalonde et al.
7,303,579 B2 12/2007 Schock et al.
7,338,516 B2 3/2008 Quincy, III et al.
7,361,186 B2 4/2008 Voorhees et al.
7,377,935 B2 5/2008 Schock et al.
7,507,250 B2 3/2009 Lennox
7,517,360 B2 4/2009 Frey et al.
RE40,815 E 6/2009 Kudaravalli et al.
7,547,320 B2 6/2009 Schook et al.
RE40,868 E 8/2009 Ryba et al.
7,621,944 B2 11/2009 Wilson et al.
7,621,945 B2 11/2009 Lennox et al.
7,666,213 B2 2/2010 Freedman, Jr. et al.
7,678,716 B2 3/2010 Yahiaoui et al.
7,686,840 B2 3/2010 Quincy, III et al.
7,727,228 B2 6/2010 Abboud et al.
7,731,739 B2 6/2010 Schock et al.
7,744,640 B1 6/2010 Faries, Jr. et al.
7,749,261 B2 7/2010 Hansen et al.
7,763,061 B2 7/2010 Schorr et al.
7,771,461 B2 8/2010 Schock et al.
7,784,304 B2 8/2010 Trinh et al.
7,799,063 B2 9/2010 Ingram et al.
7,827,815 B2 11/2010 Carson et al.
7,867,266 B2 1/2011 Collins
7,892,269 B2 2/2011 Collins et al.
7,896,910 B2 3/2011 Schirrmacher et al.
7,918,243 B2 4/2011 Diodati et al.
8,047,010 B2 11/2011 Carson et al.
8,052,624 B2 11/2011 Buchanan et al.
8,066,752 B2 11/2011 Hamilton et al.
8,182,521 B2 5/2012 Kane et al.
8,187,697 B2 5/2012 Quincy, III et al.
8,216,163 B2 * 7/2012 Edelman .................. A61F 7/02 607/108
8,283,602 B2 10/2012 Augustine et al.
8,454,671 B2 6/2013 Lennox et al.
D685,916 S 7/2013 Hoglund
8,491,644 B1 7/2013 Carson et al.
8,597,217 B2 12/2013 Lowe et al.
8,597,339 B2 12/2013 Augustine et al.
8,603,150 B2 12/2013 Kane et al.
8,632,576 B2 1/2014 Quisenberry
8,647,374 B2 2/2014 Koewler
8,715,330 B2 5/2014 Lowe et al.
8,778,119 B2 7/2014 Starr et al.
8,808,344 B2 8/2014 Scott et al.
8,840,581 B2 9/2014 McGill et al.
9,034,458 B2 5/2015 Li
9,078,742 B2 7/2015 Quincy, III et al.
9,089,462 B1 7/2015 Lafleche
9,211,358 B2 12/2015 Sinko et al.
9,278,024 B2 3/2016 Scott et al.
9,333,112 B2 5/2016 Carson
9,433,527 B2 9/2016 Varga et al.
9,552,706 B2 1/2017 Schneider, II et al.
9,566,185 B2 2/2017 Carson et al.
9,622,907 B2 4/2017 Carson et al.
9,642,404 B2 5/2017 Giles et al.
9,687,386 B2 6/2017 Carson
9,763,823 B2 9/2017 Voorhees et al.
9,907,889 B2 3/2018 Locke et al.
10,010,452 B2 7/2018 Wenske et al.
10,123,902 B2 11/2018 Carson et al.
10,220,198 B2 3/2019 Fuchs et al.
10,258,501 B2 4/2019 Carson
10,376,412 B2 8/2019 Brienza et al.
10,441,458 B2 10/2019 Voorhees et al.
10,441,707 B2 10/2019 Voorhees et al.
10,548,778 B2 2/2020 Hassenpflug et al.
D887,426 S 6/2020 Matsushita
10,912,672 B1 2/2021 Jones et al.
D922,424 S 6/2021 Frueh et al.
D925,574 S 7/2021 Beko
D928,188 S 8/2021 Giannino et al.
11,173,071 B1 11/2021 Tawil et al.
D939,550 S 12/2021 Miyai et al.
11,234,859 B2 2/2022 Voorhees et al.
D947,216 S 3/2022 Leininger
11,285,039 B2 3/2022 Steele et al.
D948,534 S 4/2022 Bessette et al.
D952,666 S 5/2022 Sajan
D959,475 S 8/2022 Norman
D960,191 S 8/2022 Feit et al.
D973,067 S 12/2022 Oh et al.
11,975,123 B2 5/2024 Appel et al.
2001/0034545 A1 10/2001 Elkins
2001/0039439 A1 11/2001 Elkins et al.
2002/0007203 A1 1/2002 Gilmartin et al.
2002/0015689 A1 2/2002 Munro et al.
2002/0107558 A1 * 8/2002 Clifton ...................... A61F 7/02 607/104
2002/0111657 A1 8/2002 Dae et al.
2002/0138121 A1 9/2002 Fox

(56) References Cited

U.S. PATENT DOCUMENTS

2002/0161419 A1 10/2002 Carson et al.
2003/0074038 A1 4/2003 Gruszecki et al.
2003/0078638 A1 4/2003 Voorhees et al.
2003/0078639 A1 4/2003 Carson
2003/0078640 A1 4/2003 Carson et al.
2003/0109911 A1 6/2003 Lachenbruch et al.
2003/0114903 A1 6/2003 Ellingboe
2003/0135252 A1 7/2003 MacHold et al.
2003/0149359 A1 8/2003 Smith
2003/0149461 A1 8/2003 Johnson
2003/0150232 A1 8/2003 Brudnicki
2003/0163179 A1 8/2003 Hoglund et al.
2003/0163180 A1 8/2003 Hoglund et al.
2003/0163183 A1 8/2003 Carson
2003/0163185 A1 8/2003 Carson
2003/0212416 A1 11/2003 Cinelli et al.
2004/0030372 A1 2/2004 Ellingboe et al.
2004/0030373 A1 2/2004 Ellingboe et al.
2004/0059212 A1 3/2004 Abreu
2004/0064170 A1 4/2004 Radons et al.
2004/0064171 A1 4/2004 Briscoe et al.
2004/0073280 A1 4/2004 Dae et al.
2004/0082886 A1 4/2004 Timpson
2004/0087606 A1 5/2004 Voorhees et al.
2004/0133253 A1 7/2004 Grahn et al.
2004/0158303 A1 8/2004 Lennox et al.
2004/0225341 A1 11/2004 Schock et al.
2004/0243122 A1 12/2004 Auth et al.
2004/0252750 A1 12/2004 Gruszecki et al.
2004/0255362 A1 12/2004 Soerens et al.
2004/0260369 A1 12/2004 Schock et al.
2004/0267339 A1 12/2004 Yon et al.
2005/0028551 A1 2/2005 Noda et al.
2005/0060012 A1 3/2005 Voorhees et al.
2005/0065583 A1 3/2005 Voorhees et al.
2005/0096714 A1 5/2005 Freedman et al.
2005/0177212 A1 8/2005 Njemanze
2005/0187502 A1 8/2005 Krempel et al.
2005/0244629 A1 11/2005 Usui et al.
2005/0288749 A1 12/2005 Lachenbruch
2006/0024053 A1 2/2006 Grant
2006/0030916 A1 2/2006 Lennox
2006/0036304 A1 2/2006 Cordani et al.
2006/0058858 A1 3/2006 Smith
2006/0069418 A1 3/2006 Schock et al.
2006/0074469 A1 4/2006 Lennox et al.
2006/0122673 A1 6/2006 Callister et al.
2006/0124141 A1 6/2006 Dobak
2006/0136023 A1 6/2006 Dobak
2006/0161232 A1 7/2006 Kasza et al.
2006/0190066 A1 8/2006 Worthen
2006/0235114 A1 10/2006 Kitazono et al.
2006/0247744 A1 11/2006 Nest et al.
2006/0276089 A1 12/2006 Amarasinghe et al.
2006/0287697 A1 12/2006 Lennox
2006/0293734 A1 12/2006 Scott et al.
2007/0016270 A1 1/2007 Stelea et al.
2007/0043409 A1 2/2007 Brian et al.
2007/0049997 A1 3/2007 Fields et al.
2007/0054122 A1 3/2007 Paisner et al.
2007/0068931 A1 3/2007 Augustine et al.
2007/0073368 A1 3/2007 Cazzini et al.
2007/0100404 A1 5/2007 Ko et al.
2007/0173735 A1 7/2007 Callister et al.
2007/0213793 A1 9/2007 Hayes
2007/0225782 A1 9/2007 Taylor
2007/0244475 A1 10/2007 Carson et al.
2007/0270925 A1 11/2007 Levinson
2008/0027523 A1 1/2008 Behringer et al.
2008/0046046 A1 2/2008 Ginsburg
2008/0114431 A1 5/2008 Ginsburg
2008/0147152 A1 6/2008 Quincy et al.
2008/0249524 A1 10/2008 Dunning
2008/0255644 A1 10/2008 Carson
2008/0269852 A1 10/2008 Lennox et al.
2008/0275534 A1 11/2008 Noel
2009/0018504 A1 1/2009 Pile-Spellman et al.
2009/0043366 A1 2/2009 Dae
2009/0066079 A1 3/2009 Miros et al.
2009/0088825 A1 4/2009 Pta
2009/0099629 A1 4/2009 Carson et al.
2009/0131835 A1 5/2009 Voorhees et al.
2009/0149925 A1 6/2009 MacDonald et al.
2009/0157000 A1 6/2009 Waller
2009/0177184 A1 7/2009 Christensen et al.
2009/0182400 A1 7/2009 Dae et al.
2009/0228082 A1 9/2009 Ross, III et al.
2009/0250367 A1 10/2009 Murdoch et al.
2009/0280182 A1 11/2009 Beck et al.
2009/0287283 A1 11/2009 Biser et al.
2009/0299287 A1 12/2009 Carson et al.
2009/0312823 A1 12/2009 Patience et al.
2009/0326619 A1 12/2009 Kagan
2010/0016933 A1 1/2010 Chen et al.
2010/0137951 A1 6/2010 Lennox et al.
2010/0168825 A1 7/2010 Barbknecht
2010/0198122 A1 8/2010 Freund
2010/0198320 A1 8/2010 Pierre et al.
2010/0204765 A1 8/2010 Hall et al.
2010/0217260 A1 8/2010 Aramayo
2010/0241073 A1 9/2010 Andersen et al.
2010/0312160 A1 12/2010 Creighton et al.
2010/0312202 A1 12/2010 Henley et al.
2011/0021960 A1 1/2011 Filtvedt et al.
2011/0029051 A1 2/2011 Ross
2011/0045056 A1 2/2011 Munro et al.
2011/0125238 A1 5/2011 Nofzinger
2011/0152982 A1 6/2011 Richardson
2011/0166633 A1 7/2011 Stull
2011/0172749 A1 7/2011 Christensen et al.
2011/0172750 A1 7/2011 Cassidy et al.
2011/0306972 A1 12/2011 Widenhouse et al.
2011/0307040 A1 12/2011 Peterson
2011/0308781 A1 12/2011 O'Riordan et al.
2011/0313497 A1 12/2011 Mcfarlane
2012/0046720 A1 2/2012 Ishizaki
2012/0065715 A1 3/2012 Carson
2012/0080031 A1 4/2012 Belson
2012/0095536 A1 4/2012 Machold et al.
2012/0172774 A1 7/2012 Lowe et al.
2012/0185021 A1 7/2012 Johnson et al.
2012/0191035 A1 7/2012 Stephan
2012/0204881 A1 8/2012 Davidson et al.
2012/0220960 A1 8/2012 Ruland
2012/0288848 A1 11/2012 Latham et al.
2013/0023808 A1 1/2013 Brown et al.
2013/0116760 A1 5/2013 Carson et al.
2013/0138185 A1 5/2013 Paxman et al.
2013/0190667 A1 7/2013 Kane et al.
2013/0238042 A1 9/2013 Gildersleeve et al.
2013/0238043 A1 9/2013 Beardall et al.
2013/0310725 A1 11/2013 Jerrells et al.
2014/0039451 A1 2/2014 Bangera et al.
2014/0046411 A1 2/2014 Elkins et al.
2014/0172050 A1 6/2014 Dabrowiak
2014/0214138 A1* 7/2014 Voorhees .................. A61F 7/10 607/104
2014/0222121 A1 8/2014 Spence et al.
2014/0228717 A1 8/2014 Parish et al.
2014/0228918 A1 8/2014 Brienza et al.
2014/0276253 A1 9/2014 Varga et al.
2014/0277301 A1 9/2014 Varga et al.
2014/0288621 A1 9/2014 Efremkin
2014/0316494 A1 10/2014 Augustine et al.
2014/0343639 A1 11/2014 Hopper et al.
2015/0025606 A1 1/2015 Davis
2015/0051673 A1 2/2015 Rivas Tapia
2015/0119963 A1 4/2015 Cosse
2015/0173942 A1 6/2015 Whitely
2015/0209174 A1 7/2015 Abreu
2015/0209192 A1 7/2015 Manion et al.
2015/0223972 A1 8/2015 Dabrowiak
2015/0230973 A1 8/2015 Dabrowiak et al.
2015/0231009 A1 8/2015 Lewis

(56) References Cited

U.S. PATENT DOCUMENTS

2015/0250643 A1 9/2015 Paradis
2015/0290042 A1 10/2015 Freer et al.
2015/0366703 A1 12/2015 Du
2015/0373781 A1 12/2015 Augustine et al.
2015/0374045 A1 12/2015 Codner et al.
2016/0008166 A1 1/2016 Voorhees et al.
2016/0022477 A1 1/2016 Schaefer et al.
2016/0038336 A1 2/2016 Hilton et al.
2016/0310316 A1 10/2016 Hixson, Jr.
2016/0324683 A1 11/2016 Carson
2017/0049618 A1 2/2017 Ward et al.
2017/0135855 A1 5/2017 Stefan et al.
2017/0151087 A1 6/2017 Carson et al.
2017/0189225 A1 7/2017 Voorhees et al.
2017/0209305 A1 7/2017 Kaforey et al.
2017/0224528 A1 8/2017 Berg et al.
2017/0246029 A1 8/2017 Clark
2017/0246031 A1 8/2017 Benyaminpour et al.
2017/0246374 A1 8/2017 Voorhees et al.
2017/0348144 A1 12/2017 Taylor et al.
2017/0348145 A1 12/2017 Voorhees et al.
2017/0354534 A1 12/2017 Paradis et al.
2018/0000255 A1 1/2018 Youngblood et al.
2018/0014967 A1 1/2018 Taylor
2018/0042762 A1 2/2018 Galer
2018/0042763 A1 2/2018 Galer et al.
2018/0064594 A1 3/2018 Finch, Jr. et al.
2018/0140407 A1 5/2018 Yoskowitz
2018/0207024 A1 7/2018 Dabrowiak et al.
2018/0214297 A1 8/2018 Hughett et al.
2018/0214302 A1 8/2018 Dabrowiak et al.
2018/0263677 A1 9/2018 Hilton et al.
2018/0263748 A1 9/2018 Quinn
2018/0295980 A1 10/2018 Boersma et al.
2018/0376539 A1 12/2018 Augustine et al.
2019/0083322 A1 3/2019 Huang et al.
2019/0085644 A1 3/2019 Ames et al.
2019/0099288 A1 4/2019 Vergara et al.
2019/0117446 A1 4/2019 Carson et al.
2019/0192337 A1 6/2019 Taylor et al.
2019/0201574 A1 7/2019 Delury et al.
2019/0262169 A1 8/2019 Vergara et al.
2019/0331277 A1 10/2019 Vachon
2020/0001022 A1 1/2020 Landy, III et al.
2020/0071051 A1 3/2020 Lewis
2020/0129326 A1 4/2020 Sinha et al.
2020/0155341 A1 5/2020 Voorhees et al.
2020/0214471 A1 7/2020 Paperno
2020/0246180 A1 8/2020 Liang et al.
2020/0345971 A1 11/2020 Schirm et al.
2020/0405530 A1 12/2020 Taylor et al.
2021/0060230 A1 3/2021 Hopper et al.
2021/0123641 A1 4/2021 Monazami et al.
2022/0087874 A1 3/2022 Schneider et al.
2022/0151821 A1 5/2022 Voorhees et al.
2022/0192865 A1 6/2022 Hughett, Sr. et al.
2022/0192867 A1 6/2022 Stich et al.
2022/0233344 A1 7/2022 Hoglund
2022/0233347 A1 7/2022 Canary et al.
2022/0265468 A1 8/2022 Xu et al.
2022/0280336 A1 9/2022 Smith et al.
2022/0287875 A1 9/2022 Minchew et al.
2022/0287876 A1 9/2022 Smith et al.
2022/0296413 A1 9/2022 Jones
2022/0296414 A1 9/2022 Bible et al.
2022/0304847 A1* 9/2022 Kuroda .................... A61F 7/08
2022/0313478 A1 10/2022 Johnston et al.
2022/0347009 A1 11/2022 Hughett, Sr. et al.
2022/0401259 A1 12/2022 Basciano et al.
2022/0406017 A1 12/2022 Wang et al.
2023/0000668 A1 1/2023 Walker et al.
2023/0009524 A1 1/2023 Johnston et al.
2023/0011631 A1 1/2023 Yin et al.
2023/0019048 A1 1/2023 Stich et al.
2023/0021245 A1 1/2023 Walker et al.
2023/0040583 A1 2/2023 Falis et al.
2023/0077318 A9 3/2023 Voorhees et al.
2023/0190519 A1 6/2023 Stich et al.
2024/0082052 A1 3/2024 Cho et al.
2024/0091054 A1 3/2024 Boone-Worthman et al.
2024/0099878 A1 3/2024 Voorhees et al.
2024/0108497 A1 4/2024 Daw et al.
2024/0366422 A1 11/2024 Johnston et al.
2025/0032310 A1 1/2025 Stich et al.
2025/0041107 A1 2/2025 Walker et al.
2025/0110628 A1 4/2025 Litman et al.
2025/0134705 A1 5/2025 Stich et al.
2025/0143918 A1 5/2025 Voorhees et al.
2025/0161107 A1 5/2025 Stich et al.
2025/0198550 A1 6/2025 Johnston et al.
2025/0332025 A1 10/2025 Brooks et al.
2026/0026965 A1 1/2026 Xu et al.
2026/0102279 A1 4/2026 Canary et al.

FOREIGN PATENT DOCUMENTS

CA 2729122 A1 7/2002
CA 2193385 C 9/2006
CN 102026596 A 4/2011
CN 101389372 B 8/2012
CN 102746518 A 10/2012
CN 103939695 B 3/2016
CN 305928532 7/2020
CN 111643265 A 9/2020
CN 306402573 3/2021
CN 113230017 A 8/2021
CN 307690236 11/2022
CN 309180016 3/2025
DE 102014118510 A1 6/2016
EP 0862901 A1 9/1998
EP 1073388 A1 2/2001
EP 1616543 A2 1/2006
EP 1641503 A2 4/2006
EP 1718894 B1 7/2010
EP 2204150 A1 7/2010
EP 2269546 A1 1/2011
GB 2118440 A 11/1983
JP H09508045 A 8/1997
JP 2002534160 A 10/2002
JP 2007029638 A 2/2007
JP 2013248293 A 12/2013
KR 20110020420 A 3/2011
WO 9807397 A1 2/1998
WO 9831310 A1 7/1998
WO 199944552 A1 9/1999
WO 9953874 A1 10/1999
WO 2000040185 A1 7/2000
WO 2003086253 A2 10/2003
WO 2004075949 A2 9/2004
WO 2005028984 A1 3/2005
WO 2005117546 A2 12/2005
WO 2007120677 A2 10/2007
WO 2009090403 A1 7/2009
WO 2009147413 A1 12/2009
WO 2009148636 A1 12/2009
WO 2012125916 A2 9/2012
WO 2012138980 A2 10/2012
WO 2015084925 A1 6/2015
WO 2016057119 A1 4/2016
WO 2016123500 A1 8/2016
WO 2017127768 A1 7/2017
WO 2018075576 A1 4/2018
WO 2022155130 A1 7/2022
WO 2022155132 A1 7/2022
WO 2022159513 A1 7/2022
WO 2022159879 A1 7/2022
WO 2022165068 A1 8/2022
WO 2022235513 A1 11/2022
WO 2023121674 A1 6/2023
WO 2023140870 A1 7/2023

(56) References Cited

FOREIGN PATENT DOCUMENTS

WO 2023154050 A1 8/2023
WO 2023229609 A1 11/2023

OTHER PUBLICATIONS

U.S. Appl. No. 17/848,074, filed Jun. 23, 2022 Advisory Action dated Jul. 9, 2024.
U.S. Appl. No. 17/848,074, filed Jun. 23, 2022 Final Office Action dated Apr. 26, 2024.
U.S. Appl. No. 18/536,087, filed Dec. 11, 2023 Non-Final Office Action dated Jun. 28, 2024.
PCT/US2022/026999 filed Apr. 29, 2022 International Search Report and Written Opinion dated Oct. 24, 2022.
U.S. Appl. No. 17/589,849, filed Jan. 31, 2022 Notice of Allowance dated Aug. 23, 2023.
U.S. Appl. No. 17/848,074, filed Jun. 23, 2022 Non-Final Office Action dated Nov. 30, 2023.
Advantage Engineering, "Proper Use of Inhibited Propylene Glycol", Jun. 12, 2001, http://www.ttequip.com/knowledgelibrary/Proper%20Use%20Of%20Inh- ibited%20Propylene%20Glycol.pdf Jun. 12, 2001.
Hyperphysicis, "Thermal Conductivity", available Jul. 31, 2010, https://web.archive.org/web/20100731025127/http://hyperphysics.phy-astr.g- us.edu/hbase/tables.thrcn.html Jul. 31, 2010.
Murray, R. Z., et al. "Development and use of biomaterials as wound healing therapies" Burns & Trauma (2019) 7:2 https://doi.org/10.1186/s41038-018-0139-7 (2019).
P21TUS2022011971 filed Jan. 11, 2022 International Search Report and Written Opinion dated Apr. 21, 2022.
PCT/US2015/045548 filed Aug. 17, 2015 International Search Report and Written Opinion dated Nov. 24, 2015.
PCT/US2016/015688 filed Jan. 29, 2016 International Search Report and Written Opinion dated Apr. 1, 2016.
PCT/US2022/011980 filed Jan. 11, 2022 International Search Report and Written Opinion dated Apr. 13, 2022.
PCT/US2022/013007 filed Jan. 19, 2022 International Search Report and Written Opinion dated Apr. 22, 2022.
PCT/US2022/013672 filed Jan. 25, 2022, International Search Report and Written Opinion dated Jul. 15, 2022.
PCT/US2022/014147 filed Jan. 27, 2022 International Search Report and Written Opinion dated Jul. 18, 2022.
Sevgi, M., et al. "Topical Antimicrobials for Burn Infections—An Update" Recent Pat Antiinfect Drug Discov. Dec. 2013 ; 8(3): 161-197.
Stoica, A. E., et al. "Hydrogel Dressings for the Treatment of Burn Wounds: An Up-To-Date Overview" Materials 2020, 13, 2853; doi:10.3390/ma13122853. (2020).
U.S. Appl. No. 15/512,025, filed Mar. 16, 2017 Final Office Action dated Jun. 25, 2020.
U.S. Appl. No. 15/512,025, filed Mar. 16, 2017 Non-Final Office Action dated Jul. 18, 2019.
U.S. Appl. No. 16/597,393, filed Oct. 9, 2019 Corrected Notice of Allowability dated Nov. 18, 2021.
U.S. Appl. No. 16/597,393, filed Oct. 9, 2019 Non-Final Office Action dated Apr. 28, 2021.
U.S. Appl. No. 17/589,849, filed Jan. 31, 2022 Final Office Action dated Jun. 27, 2023.
U.S. Appl. No. 17/589,849, filed Jan. 31, 2022 Non-Final Office Action dated Apr. 12, 2023.
PCT/US2022/013569 filed Jan. 24, 2022 International Search Report and Written Opinion dated Aug. 29, 2022.
PCT/US2022/016020 filed Feb. 10, 2022 International Search Report and Written Opinion dated Oct. 31, 2022.
U.S. Appl. No. 17/547,128, filed Dec. 9, 2021 Restriction Requirement dated Sep. 5, 2024.
U.S. Appl. No. 17/583,090, filed Jan. 24, 2022 Restriction Requirement dated Sep. 6, 2024.
U.S. Appl. No. 17/686,301, filed Mar. 3, 2022 Non-Final Office Action dated Oct. 1, 2024.
U.S. Appl. No. 17/689,791, filed Mar. 8, 2022 Restriction Requirement dated Oct. 16, 2024.
U.S. Appl. No. 17/691,990, filed Mar. 10, 2022 Restriction Requirement dated Oct. 16, 2024.
U.S. Appl. No. 17/709,019, filed Mar. 30, 2022 Restriction Requirement dated Oct. 16, 2024.
U.S. Appl. No. 17/723,210, filed Apr. 18, 2022 Restriction Requirement dated Oct. 16, 2024.
U.S. Appl. No. 17/848,074, filed Jun. 23, 2022 Non-Final Office Action dated Aug. 15, 2024.
U.S. Appl. No. 18/536,087, filed Dec. 11, 2023 Notice of Allowance dated Aug. 29, 2024.
PCT/US2022/031428 filed May 27, 2022 International Search Report and Written Opinion dated Jan. 30, 2023.
U.S. Appl. No. 17/547,128, filed Dec. 9, 2021 Non-Final Office Action dated Feb. 10, 2025.
U.S. Appl. No. 17/552,309, filed Dec. 15, 2021 Non-Final Office Action dated Mar. 14, 2025.
U.S. Appl. No. 17/552,309, filed Dec. 15, 2021 Restriction Requirement dated Dec. 12, 2024.
U.S. Appl. No. 17/583,090, filed Jan. 24, 2022 Non-Final Office Action dated Feb. 13, 2025.
U.S. Appl. No. 17/584,101, filed Jan. 25, 2022 Non-Final Office Action dated Feb. 5, 2025.
U.S. Appl. No. 17/584,101, filed Jan. 25, 2022 Restriction Requirement dated Nov. 5, 2024.
U.S. Appl. No. 17/678,965, filed Feb. 23, 2022 Non-Final Office Action dated Feb. 12, 2025.
U.S. Appl. No. 17/686,301, filed Mar. 3, 2022 Final Office Action dated Jan. 29, 2025.
U.S. Appl. No. 17/689,791, filed Mar. 8, 2022 Non-Final Office Action dated Dec. 30, 2024.
U.S. Appl. No. 17/690,908, filed Mar. 9, 2022 Non-Final Office Action dated Dec. 18, 2024.
U.S. Appl. No. 17/691,990, filed Mar. 10, 2022 Non-Final Office Action dated Dec. 17, 2024.
U.S. Appl. No. 17/694,416, filed Mar. 14, 2022 Non-Final Office Action dated Jan. 22, 2025.
U.S. Appl. No. 17/694,416, filed Mar. 14, 2022 Restriction Requirement dated Nov. 8, 2024.
U.S. Appl. No. 17/700,216, filed Mar. 21, 2022 Non-Final Office Action dated Feb. 5, 2025.
U.S. Appl. No. 17/709,019, filed Mar. 30, 2022 Non-Final Office Action dated Dec. 31, 2024.
U.S. Appl. No. 17/723,210, filed Apr. 18, 2022 Non-Final Office Action dated Dec. 20, 2024.
U.S. Appl. No. 17/848,074, filed Jun. 23, 2022 Notice of Allowance dated Nov. 26, 2024.
U.S. Appl. No. 17/849,419, filed Jun. 24, 2022 Final Office Action dated Feb. 14, 2025.
U.S. Appl. No. 17/849,419, filed Jun. 24, 2022 Non-Final Office Action dated Nov. 8, 2024.
U.S. Appl. No. 17/857,997, filed Jul. 5, 2022 Restriction Requirement dated Feb. 12, 2025.
U.S. Appl. No. 17/859,995, filed Jul. 7, 2022 Non-Final Office Action dated Mar. 11, 2025.
U.S. Appl. No. 17/881,270, filed Aug. 4, 2022 Restriction Requirement dated Feb. 11, 2025.
All in 1: Injection Tracker, posted date unavailable [online], [retrieved Apr. 10, 2025]. Retrieved from internet, https://apps.apple.com/us/app/all-in-1-injection-tracker/id1667540577. (Year: 2025).
Creating an accessible, usable and compelling Injection Site Tracking feature that can used by all our users, posted date May 2020 [u online], [retrieved Apr. 10, 2025]. Retrieved from internet, https://www.bradstricker.com/case-studies/injection-site-tracking. (Year: 2020).
Injection Tracker App, posted date unavailable [online], [retrieved Apr. 10, 2025]. Retrieved from internet, https://www.vladcristei.com/project_page_it. (Year: 2025).
U.S. Appl. No. 17/583,090, filed Jan. 24, 2022 Final Office Action dated Jul. 1, 2025.

(56) References Cited

OTHER PUBLICATIONS

U.S. Appl. No. 17/678,965, filed Feb. 23, 2022 Notice of Allowance dated Jun. 3, 2025.
U.S. Appl. No. 17/686,301, filed Mar. 3, 2022 Advisory Action dated Apr. 4, 2025.
U.S. Appl. No. 17/686,301, filed Mar. 3, 2022 Non-Final Office Action dated May 14, 2025.
U.S. Appl. No. 17/689,791, filed Mar. 8, 2022 Final Office Action dated May 21, 2025.
U.S. Appl. No. 17/690,908, filed Mar. 9, 2022 Final Office Action dated Jun. 24, 2025.
U.S. Appl. No. 17/694,416, filed Mar. 14, 2022 Final Office Action dated Jun. 20, 2025.
U.S. Appl. No. 17/700,216, filed Mar. 21, 2022 Final Office Action dated Jun. 23, 2025.
U.S. Appl. No. 17/709,019, filed Mar. 30, 2022 Final Office Action dated Jun. 15, 2025.
U.S. Appl. No. 17/723,210, filed Apr. 18, 2022 Final Office Action dated May 21, 2025.
U.S. Appl. No. 17/849,419, filed Jun. 24, 2022 Non-Final Office Action dated Jun. 13, 2025.
U.S. Appl. No. 17/857,997, filed Jul. 5, 2022 Non-Final Office Action dated Apr. 28, 2025.
U.S. Appl. No. 17/881,270, filed Aug. 4, 2022 Non-Final Office Action dated Apr. 28, 2025.
U.S. Appl. No. 18/085,566, filed Dec. 20, 2022 Restriction Requirement dated May 16, 2025.
U.S. Appl. No. 29/939,277, filed Apr. 25, 2024 Non-Final Office Action dated May 13, 2025.
Wound care app can help determine appropriate wounddressings, posted date Apr. 24, 2013 [online], [retrieved Apr. 10, 2025]. Retrieved from internet, https://www.imedicalapps.com/2013/04/wound-care-app-dressings/. (Year: 2013).
Lustig et al. "Solute Diffusion in Swollen Membranes. IX. Scaling Laws for Solute Diffusion in Gels", Journal of Applied Polymer Science, vol. 36, pp. 735-747 (Year: 1988).
U.S. Appl. No. 17/547,128, filed Dec. 9, 2021 Final Office Action dated Aug. 27, 2025.
U.S. Appl. No. 17/552,309, filed Dec. 15, 2021 Advisory Action dated Oct. 2, 2025.
U.S. Appl. No. 17/552,309, filed Dec. 15, 2021 Final Office Action dated Jul. 30, 2025.
U.S. Appl. No. 17/583,090, filed Jan. 24, 2022 Notice of Allowance dated Sep. 30, 2025.
U.S. Appl. No. 17/584,101, filed Jan. 25, 2022 Final Office Action dated Oct. 23, 2025.
U.S. Appl. No. 17/686,301, filed Mar. 3, 2022 Final Office Action dated Oct. 28, 2025.
U.S. Appl. No. 17/689,791, filed Mar. 8, 2022 Advisory Action dated Jul. 24, 2025.
U.S. Appl. No. 17/690,908, filed Mar. 9, 2022 Advisory Action dated Sep. 3, 2025.
U.S. Appl. No. 17/690,908, filed Mar. 9, 2022 Non-Final Office Action dated Oct. 2, 2025.
U.S. Appl. No. 17/691,990, filed Mar. 10, 2022 Advisory Action dated Jul. 24, 2025.
U.S. Appl. No. 17/691,990, filed Mar. 10, 2022 Non-Final Office Action dated Aug. 28, 2025.
U.S. Appl. No. 17/694,416, filed Mar. 14, 2022 Advisory Action dated Aug. 20, 2025.
U.S. Appl. No. 17/694,416, filed Mar. 14, 2022 Non-Final Office Action dated Oct. 1, 2025.
U.S. Appl. No. 17/697,879, filed Mar. 17, 2022 Non-Final Office Action dated Sep. 30, 2025.
U.S. Appl. No. 17/700,216, filed Mar. 21, 2022 Advisory Action dated Oct. 9, 2025.
U.S. Appl. No. 17/709,019, filed Mar. 30, 2022 Advisory Action dated Jul. 24, 2025.
U.S. Appl. No. 17/723,210, filed Apr. 18, 2022 Advisory Action dated Jul. 31, 2025.
U.S. Appl. No. 17/848,039, filed Jun. 23, 2021 Non-Final Office Action dated Jul. 29, 2025.
U.S. Appl. No. 17/857,997, filed Jul. 5, 2022 Final Office Action dated Oct. 27, 2025.
U.S. Appl. No. 17/859,995, filed Jul. 7, 2022 Advisory Action dated Oct. 28, 2025.
U.S. Appl. No. 17/859,995, filed Jul. 7, 2022 Final Office Action dated Aug. 22, 2025.
U.S. Appl. No. 17/881,270, filed Aug. 4, 2022 Final Office Action dated Oct. 27, 2025.
U.S. Appl. No. 18/085,566, filed Dec. 20, 2022 Non-Final Office Action dated Oct. 1, 2025.
U.S. Appl. No. 18/274,156, filed Jul. 25, 2023 Non-Final Office Action dated Oct. 1, 2025.
U.S. Appl. No. 18/274,436, filed Jul. 26, 2023 Non-Final Office Action dated Oct. 1, 2025.
U.S. Appl. No. 29/939,277, filed Apr. 25, 2024 Restriction Requirement dated Oct. 2, 2025.
U.S. Appl. No. 17/547,128, filed Dec. 9, 2021 Advisory Action dated Nov. 19, 2025.
U.S. Appl. No. 17/547,128, filed Dec. 9, 2021 Non-Final Office Action dated Dec. 29, 2025.
U.S. Appl. No. 17/552,309, filed Dec. 15, 2021 Non-Final Office Action dated Nov. 5, 2025.
U.S. Appl. No. 17/686,301, filed Mar. 3, 2022 Advisory Action dated Jan. 14, 2026.
U.S. Appl. No. 17/689,791, filed Mar. 8, 2022 Non-Final Office Action dated Nov. 5, 2025.
U.S. Appl. No. 17/700,216, filed Mar. 21, 2022 Non-Final Office Action dated Dec. 3, 2025.
U.S. Appl. No. 17/709,019, filed Mar. 30, 2022 Non-Final Office Action dated Nov. 19, 2025.
U.S. Appl. No. 17/723,210, filed Apr. 18, 2022 Non-Final Office Action dated Dec. 29, 2025.
U.S. Appl. No. 17/848,039, filed Jun. 23, 2022 Final Office Action dated Dec. 29, 2025.
U.S. Appl. No. 17/849,419, filed Jun. 24, 2022 Notice of Allowance dated Jan. 29, 2026.
U.S. Appl. No. 17/859,995, filed Jul. 7, 2022 Non-Final Office Action dated Dec. 23, 2025.
U.S. Appl. No. 17/881,270, filed Aug. 4, 2022 Advisory Action dated Jan. 14, 2026.
U.S. Appl. No. 18/272,332, filed Jul. 13, 2023 Restriction Requirement dated Jan. 21, 2026.
U.S. Appl. No. 18/273,163, filed Jul. 19, 2023 Non-Final Office Action dated Feb. 3, 2026.
U.S. Appl. No. 18/273,163, filed Jul. 19, 2023 Restriction Requirement dated Nov. 6, 2025.
U.S. Appl. No. 18/289,341, filed Nov. 2, 2023 Restriction Requirement dated Nov. 6, 2025.
U.S. Appl. No. 18/715,504, filed May 31, 2024 Restriction Requirement dated Feb. 4, 2026.
U.S. Appl. No. 19/068,969, filed Mar. 3, 2025 Non-Final Office Action dated Dec. 29, 2025.
U.S. Appl. No. 17/547,128, filed Dec. 9, 2021 Final Office Action dated Apr. 6, 2026.
U.S. Appl. No. 17/552,309, filed Dec. 15, 2021 Final Office Action dated Apr. 22, 2026.
U.S. Appl. No. 17/686,301, filed Mar. 3, 2022 Non-Final Office Action dated Apr. 3, 2026.
U.S. Appl. No. 17/689,791, filed Mar. 8, 2022 Final Office Action dated Apr. 22, 2026.
U.S. Appl. No. 17/691,990, filed Mar. 10, 2022 Final Office Action dated Mar. 9, 2026.
U.S. Appl. No. 17/694,416, filed Mar. 14, 2022 Final Office Action dated Apr. 9, 2026.
U.S. Appl. No. 17/697,879, filed Mar. 17, 2022 Non-Final Office Action dated Mar. 26, 2026.
U.S. Appl. No. 17/709,019, filed Mar. 30, 2022 Final Office Action dated Apr. 22, 2026.
U.S. Appl. No. 17/837,956, filed Jun. 10, 2022 Final Office Action dated Feb. 24, 2026.

(56) References Cited

OTHER PUBLICATIONS

U.S. Appl. No. 17/848,039, filed Jun. 23, 2022 Notice of Allowance dated Apr. 13, 2026.
U.S. Appl. No. 18/085,566, filed Dec. 20, 2022 Final Office Action dated Mar. 9, 2026.
U.S. Appl. No. 18/272,332, filed Jul. 13, 2023 Non-Final Office Action dated Mar. 25, 2026.
U.S. Appl. No. 18/274,156, filed Jul. 25, 2023 Final Office Action dated Mar. 25, 2026.
U.S. Appl. No. 18/274,436, filed Jul. 26, 2023 Final Office Action dated Mar. 25, 2026.
U.S. Appl. No. 18/289,341, filed Nov. 2, 2023 Non-Final Office Action dated Feb. 18, 2026.
U.S. Appl. No. 18/715,504, filed May 31, 2024 Non-Final Office Action dated Apr. 9, 2026.
U.S. Appl. No. 18/832,782, filed Jul. 24, 2024 Non-Final Office Action dated Apr. 20, 2026.
U.S. Appl. No. 18/837,098, filed Aug. 8, 2024 Final Office Action dated Apr. 22, 2026.
U.S. Appl. No. 29/939,277, filed Apr. 25, 2024 Ex Parte Quayle Action dated Feb. 23, 2026.

* cited by examiner

100
FLUID DELIVERY LINE
130
111
236
237
110
230
232
CIRCULATING CIRCUIT
240
SUPPLY TANK
241
235
238
FLOW SENSOR
231
CIRCULATION PUMP
112
224
CIRCULATION TANK
HEATER
227
228
225
222
MIXING CIRCUIT
MIXING PUMP
221
112
215
213
CHILLER TANK
CHILLER PUMP
211
214
CHILLER
CHILLER CIRCUIT
212
210

120
150
460
455
130

120
410
420
430
422
421
150
460
461
423
130
112
112
50

600
601
611
611
610
610
630
130

600
610
51
50
130
630
610

735
730
735
730
715
710

720
730
730
715
710
735
735

721
720
7B
715
710
711
130

820
817
815
810
130

820
817
817
815
810
130

930
958
950
954
953
963
956
961
925
957
955
962
951
952
943
941

947
942
912
944
946
940
954
953
930
958
950
963
956
961
925
957
943
922
941

962
955
912
944
946
942
952
940

PAD DESIGNS TO IMPROVE DELIVERY OF TEMPERATURE THERAPY

PRIORITY

This application is a U.S. national stage application of International Application No. PCT/US2022/011980, filed Jan. 11, 2022, which claims the benefit of priority to U.S. Provisional Application No. 63/136,335, filed Jan. 12, 2021, each of which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g. water) through one or more thermal contact pads coupled to a patient to affect surface-to-surface thermal energy exchange with the patient. In general, TTM systems comprise a TTM fluid control module coupled to at least one contact pad via a fluid deliver line. One such TTM system is disclosed in U.S. Pat. No. 6,645,232, titled "Patient Temperature Control System with Fluid Pressure Maintenance" filed Oct. 11, 2001 and one such thermal contact pad and related system is disclosed in U.S. Pat. No. 6,197,045 titled "Cooling/heating Pad and System" filed Jan. 4, 1999, both of which are incorporated herein by reference in their entireties. As noted in the '045 patent, the ability to establish and maintain intimate pad-to-patient contact is of importance to fully realizing medical efficacies with TTM systems.

As these and other medical applications have evolved, the accommodation of different patient sizes has become more important. Disclosed herein are embodiments of devices and methods for the adjusting the patient contact area of the thermal pad to better accommodate patients of different sizes.

SUMMARY OF THE INVENTION

Briefly summarized, disclosed herein is a medical pad for exchanging thermal energy between a targeted temperature management (TTM) fluid and a patient. The pad may comprise a fluid containing layer for containing the TTM fluid, where the fluid containing layer comprises a fluid inlet and a fluid outlet and where the TTM fluid is circulatable within the fluid containing layer from the fluid inlet to the fluid outlet. The pad may further comprise a patient contact surface defining a patient contact area to facilitate thermal energy exchange with the patient and the patient contact area may be convertible from a first patient contact area to a second patient contact area, where the second patient contact area is different from the first patient contact area.

In some embodiments, the second patient contact area is at least 10 percent greater than the first patient contact area. The patient contact area may be expandable from the first patient contact area to the second patient contact area and in some embodiments, the patient contact area is expandable along a single dimension. The pad may comprise one or more folds to facilitate expansion from the first patient contact area to the second patient contact area patient and in some embodiments, the pad comprises a stretchable material to facilitate expansion from the first patient contact area to the second patient contact area.

In some embodiments, the pad may further comprise a first pad defining the first patient contact area and a second pad connectable to the first pad and the second pad includes a separate second patient contact area, and converting the first patient contact area to the second patient contact area may comprise connecting the second pad to the first pad thereby combining the first patient contact area with the separate second patient contact area to the define the second patient contact area. The first pad includes a first fluid containing layer, the second pad includes a second fluid containing layer, and connecting the second pad to the first pad may include fluidly coupling the second fluid containing layer to the fluid containing layer so that the TTM fluid is circulatable within the second fluid containing layer.

In some embodiments, converting the first patient contact area to the second patient contact area comprises separating a removable portion of the pad from a remaining portion of the pad. The removable portion may be disposed along an entire circumference of the remaining portion or a partial perimeter of the remaining portion. The removable portion comprises a removable fluid containing layer, the remaining portion comprises a remaining fluid containing layer, and the pad comprises one or more fluid conduits extending between the remaining fluid containing layer and the removable fluid containing layer. In some embodiments, converting the first patient contact area to the second patient contact area comprises separating a removable portion of the one or more conduits from a remaining portion of the one or more conduits and occluding the remaining portion of the one or more fluid conduits.

In some embodiments, the pad is configured to be disposed on a bed surface, and the first contact area is defined by a portion of the pad disposed between the patient and the bed surface. The pad may comprise one or more lateral extensions extending away from the patient along the bed surface, and converting the first contact area to the second contact area comprises wrapping at least a portion of the one or more lateral extensions around a portion of the patient to define the second contact area. The portion of the patient may comprise at least a portion of a torso of the patient. The pad may comprise one or more straps to secure the one or more lateral extensions around the portion of the patient.

In some embodiments, The thermal pad comprises a first portion of the pad including a first portion of the patient contact area is separable from a second portion of the pad comprising a second portion of the patient contact area, and wherein the first portion of the pad is coupled to the second portion of the pad via an extendable member. The extendable member comprises one or more fluid conduits extending between the first portion of the pad and the second portion of the pad.

In some embodiments, the fluid containing layer comprises a TTM fluid flow path, and the pad further comprises a filter disposed in line with the TTM fluid flow path.

Disclosed herein is also a method of providing a targeted temperature management (TTM) therapy to a patient. The method comprises providing a TTM system comprising that includes a TTM module configured to provide a TTM fluid, a thermal pad configured to receive the TTM fluid from the TTM module to facilitate thermal energy transfer between the TTM fluid and a patient, and a fluid delivery line (FDL) extending between the TTM module and the FDL is configured to provide TTM fluid flow between the TTM module and the thermal pad. The thermal pad comprises a patient contact surface defining a patient contact area to facilitate thermal energy exchange with the patient and the patient contact area is convertible from a first patient contact area to a second patient contact area, wherein the second patient contact area is different from the first patient contact area. The method further includes applying the pad to the patient and delivering TTM fluid from the TTM module to the thermal pad.

The method may comprise expanding the pad along a single dimension to convert the first patient contact area to the second patient contact area. The method may comprise stretching a material of the pad to convert the first patient contact area to the second patient contact area. The method may comprise coupling a second thermal pad to the first thermal pad, where the first thermal pad defines the first patient contact area, and the first patient contact area is combined with a separate second patient contact area of the second thermal pad to define the second patient contact area. The method may comprise separating a removable portion of the thermal pad from a remaining portion of the thermal pad to convert the first patient contact area to the second patient contact area.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. The words "including," "has," and "having," as used herein, including the claims, shall have the same meaning as the word "comprising." Furthermore, the terms "or" and "and/or" as used herein are to be interpreted as inclusive or meaning any one or any combination. As an example, "A, B or C" or "A, B and/or C" mean "any of the following: A; B; C; A and B; A and C; B and C; A, B and C." An exception to this definition will occur only when a combination of elements, components, functions, steps or acts are in some way inherently mutually exclusive.

The phrases "connected to" and "coupled to" refer to any form of interaction between two or more entities, including mechanical, electrical, magnetic, electromagnetic, fluid, signal, communicative (including wireless), and thermal interaction. Two components may be connected or coupled to each other even though they are not in direct contact with each other. For example, two components may be coupled to each other through an intermediate component.

Unless defined otherwise, all technical and scientific terms used herein have the same meaning as commonly understood by those of ordinary skill in the art.

Figure 1:
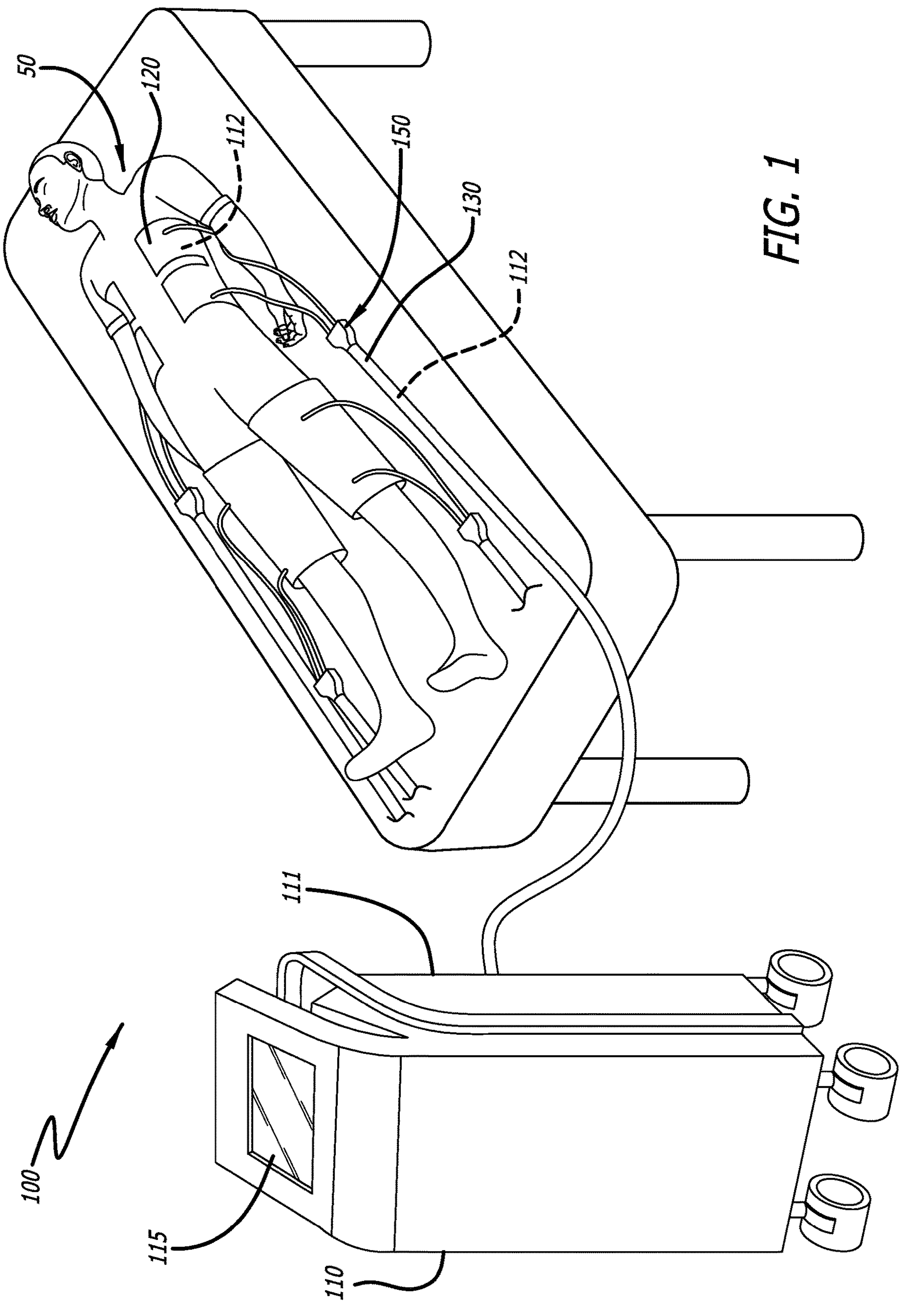
FIG. 1 illustrates a targeted temperature management (TTM) system for cooling or warming a patient, in accordance with some embodiments.

FIG. 1 illustrates a targeted temperature management (TTM) system 100 connected to a patient 50 for administering targeted temperature management therapy to the patient 50 which may include a cooling and/or warming of the patient 50, in accordance with some embodiments. The TTM system 100 comprises a TTM module 110 including a graphical user interface (GUI) 115 enclosed within a module housing 111. The TTM system 100 includes a fluid deliver line (FDL) 130 extending from the TTM module 110 to a thermal contact pad assembly 120 to provide for flow of TTM fluid 112 between the TTM module 110 and the pad assembly 120. The FDL includes two conduits to facilitate delivery flow of TTM fluid 112 from the TTM module 110 to the pad assembly 120 and return flow TTM fluid 112 from the pad assembly 120 to the TTM module 110. In some embodiments, the two conduits may be attached to each other along a portion of a length of the FDL.

The TTM system 100 may include 1, 2, 3, 4 or more pads 120 and the TTM system 100 may include 1, 2, 3, 4 or more fluid delivery lines 130. In use, the TTM module 110 prepares the TTM fluid 112 for delivery to the pad assembly 120 by heating or cooling the TTM fluid 112 to a defined temperature in accordance with a prescribed TTM therapy. The TTM module 110 circulates the TTM fluid 112 along a TTM fluid flow path including within the pad assembly 120 to facilitate thermal energy exchange with the patient 50. During the TTM therapy, the TTM module 110 may continually control the temperature of the TTM fluid 112 toward a target TTM temperature.

The TTM system 100 may include a connector system 150 to couple the FDL 130 to the pad assembly 120. In some embodiments, the connector system 150 may couple a single fluid conduit of the FDL to the pad assembly 120. Hence, the connection between the FDL 130 and the pad assembly 120 may comprise more than one connector system 150 to couple more than one fluid conduit to the pad assembly 120. The connector system 150 is further described below in FIGS. 4A and 4B.

Figure 2:
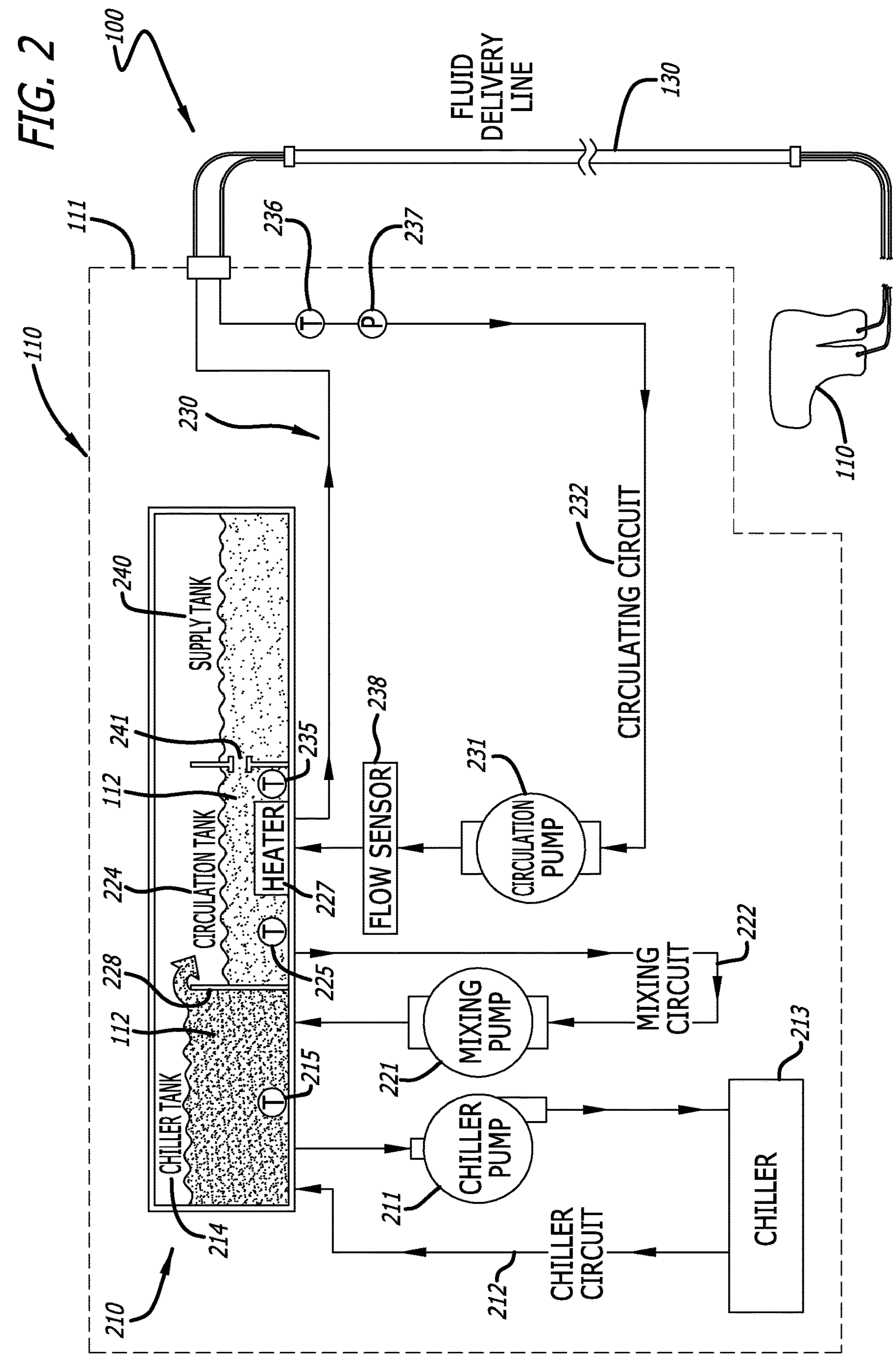
FIG. 2 illustrates a hydraulic schematic of the TTM system of FIG. 1, in accordance with some embodiments.

FIG. 2 illustrates a hydraulic schematic of the TTM system 100. The FDL 130 and the pad assembly 120 are disposed external to the housing 111 of the TTM module 110. The TTM module includes various fluid sensors and fluid control devices to prepare and circulate the TTM fluid 112. The fluid subsystems of the TTM module may include a temperature control subsystem 210 and a circulation subsystem 230.

The temperature control subsystem 210 may include a chiller pump 211 to pump (recirculate) TTM fluid 112 through a chiller circuit 212 that includes a chiller 213 and a chiller tank 214. A temperature sensor 215 within the chiller tank 214 is configured to measure a temperature of the TTM fluid 112 within the chiller tank 214. The chiller 213 may be controlled by a temperature control logic (see FIG. 3) as further described below to establish a desired temperature of the TTM fluid 112 within chiller tank 214. In some instances, the temperature of the TTM fluid 112 within the chiller tank 214 may be less than the target temperature for the TTM therapy.

The temperature control subsystem 210 may further include a mixing pump 221 to pump TTM fluid 112 through a mixing circuit 222 that includes the chiller tank 214, a circulation tank 224, and a dam 228 disposed between the chiller tank 214 and circulation tank 224. The TTM fluid 112, when pumped by the mixing pump 221, enters the chiller tank 214 and mixes with the TTM fluid 112 within the chiller tank 214. The mixed TTM fluid 112 within the chiller tank 214 flows over the dam 228 and into the circulation tank 224. In other words, the mixing circuit 222 mixes the TTM fluid 112 within chiller tank 214 with the TTM fluid 112 within circulation tank 224 to cool the TTM fluid 112 within the circulation tank 224. A temperature sensor 225 within the circulation tank 224 measures the temperature of the TTM fluid 112 within the circulation tank 224. The temperature control logic may control the mixing pump 221 in accordance with temperature data from the temperature sensor 225 within the circulation tank 224.

The circulation tank 224 includes a heater 227 to increase to the temperature of the TTM fluid 112 within the circulation tank 224, and the heater 227 may be controlled by the temperature control logic. In summary, the temperature control logic when executed by the processor (see FIG. 3) may 1) receive temperature data from the temperature sensor 215 within the chiller tank and the temperature sensor 225 within the circulation tank 224 and 2) control the operation of the chiller 213, the chiller pump 211, the heater 227, and mixing pump 222 to establish and maintain the temperature of the TTM fluid 112 within the circulation tank 224 at the target temperature for the TTM therapy.

The circulation subsystem 230 comprises a circulation pump 213 to pull TTM fluid 112 from the circulation tank 224 and through a circulating circuit 232 that includes the fluid delivery line 130 and the pad assembly 120 located upstream of the circulation pump 213. The circulating circuit 232 also includes a pressure sensor 237 to represent a pressure of the TTM fluid 112 within the pad assembly 120. The circulating circuit 232 includes a temperature sensor 235 within the circulation tank 224 to represent the temperature of the TTM fluid 112 entering the pad assembly 120 and a temperature sensor 236 to represent the temperature of the TTM fluid exiting the pad assembly 120. A flow meter 238 is disposed downstream of the circulation pump 213 to measure the flow rate of TTM fluid 112 through the circulating circuit 232 before the TTM fluid 112 re-enters that the circulation tank 224.

In use, the circulation tank 224, which may be vented to atmosphere, is located below (i.e., at a lower elevation than) the pad assembly 120 so that a pressure within the pad assembly 120 is less than atmospheric pressure (i.e., negative) when TTM fluid flow through the circulating circuit 232 is stopped. The pad assembly 120 is also placed upstream of the circulation pump 231 to further establish a negative pressure within the pad assembly 120 when the circulation pump 213 is operating. The fluid flow control logic (see FIG. 3) may control the operation of the circulation pump 213 to establish and maintain a desired negative pressure within the pad assembly 120. A supply tank 240 provides TTM fluid 112 to the circulation tank 224 via a port 241 to maintain a defined volume of TTM fluid 112 within the circulation tank 224.

Figure 3:
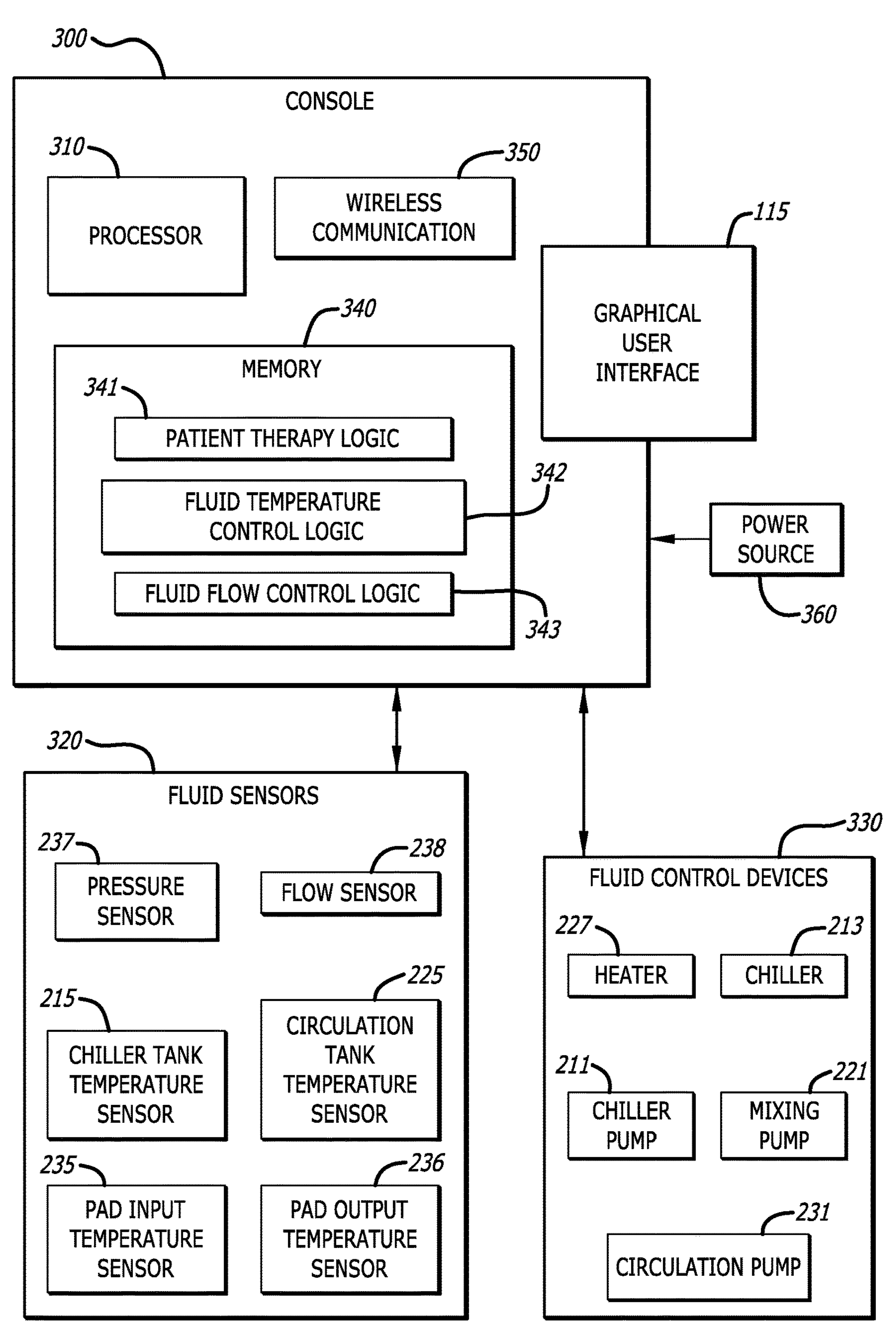
FIG. 3 illustrates a block diagram depicting various elements of a console of the TTM module of FIG. 1, in accordance with some embodiments.

FIG. 3 illustrates a block diagram depicting various elements of the TTM module 110 of FIG. 1, in accordance with some embodiments. The TTM module 110 includes a console 300 including a processor 310 and memory 340 including non-transitory, computer-readable medium. Logic modules stored in the memory 340 include patient therapy logic 341, fluid temperature control logic 342, and fluid flow control logic 343. The logic modules when executed by the processor 310 define the operations and functionality of the TTM Module 110.

Illustrated in the block diagram of FIG. 3 are fluid sensors 320 as described above in relation to FIG. 2. Each of the fluid sensors 320 are coupled to the console 300 so that data from the fluid sensors 320 may be utilized in the performance of TTM module operations. Fluid control devices 330 are also illustrated in FIG. 3 as coupled to the console 300. As such, logic modules may control the operation of the fluid control devices 330 as further described below.

The patient therapy logic 341 may receive input from the clinician via the GUI 115 to establish operating parameters in accordance with a prescribed TTM therapy. Operating parameters may include a target temperature for the TTM fluid 112 and/or a thermal energy exchange rate which may comprise a time-based target temperature profile. In some embodiments, the fluid temperature control logic 342 may define other fluid temperatures of the TTM fluid 112 within the TTM module 110, such a target temperature for the TTM fluid 112 within the chiller tank 214, for example.

The fluid temperature control logic 342 may perform operations to establish and maintain a temperature of the TTM fluid 112 delivered to the pad assembly 120 in accordance with the predefined target temperature. One temperature control operation may include chilling the TTM fluid 112 within the chiller tank 214. The fluid temperature control logic 342 may utilize temperature data from the chiller tank temperature sensor 215 to control the operation of the chiller 213 to establish and maintain a temperature of the TTM fluid 112 within the chiller tank 214.

Another temperature control operation may include cooling the TTM fluid 112 within the circulation tank 224. The fluid temperature control logic 342 may utilize temperature data from the circulation tank temperature sensor 225 to control the operation of the mixing pump 221 to decrease the temperature of the TTM fluid 112 within the circulation tank 224 by mixing TTM fluid 112 from the chiller tank 214 with TTM fluid 112 within circulation tank 224.

Still another temperature control operation may include warming the TTM fluid 112 within the circulation tank 224. The fluid temperature control logic 342 may utilize temperature data from the circulation tank temperature sensor 225 to control the operation of the heater 227 to increase the temperature of the TTM fluid 112 within the circulation tank 224.

The fluid flow control logic 343 may control the operation of the circulation pump 231. As a thermal energy exchange rate is at least partially defined by the flow rate of the TTM fluid 112 through the pad assembly 120, the fluid flow control logic 343 may, in some embodiments, control the operation of the circulation pump 231 in accordance with a defined thermal energy exchange rate for the TTM therapy.

The console 300 may include or be couple do wireless communication module 350 to facilitate wireless communication with external devices. A power source 360 provides electrical power to the console 300.

Figures 4A, 4B:
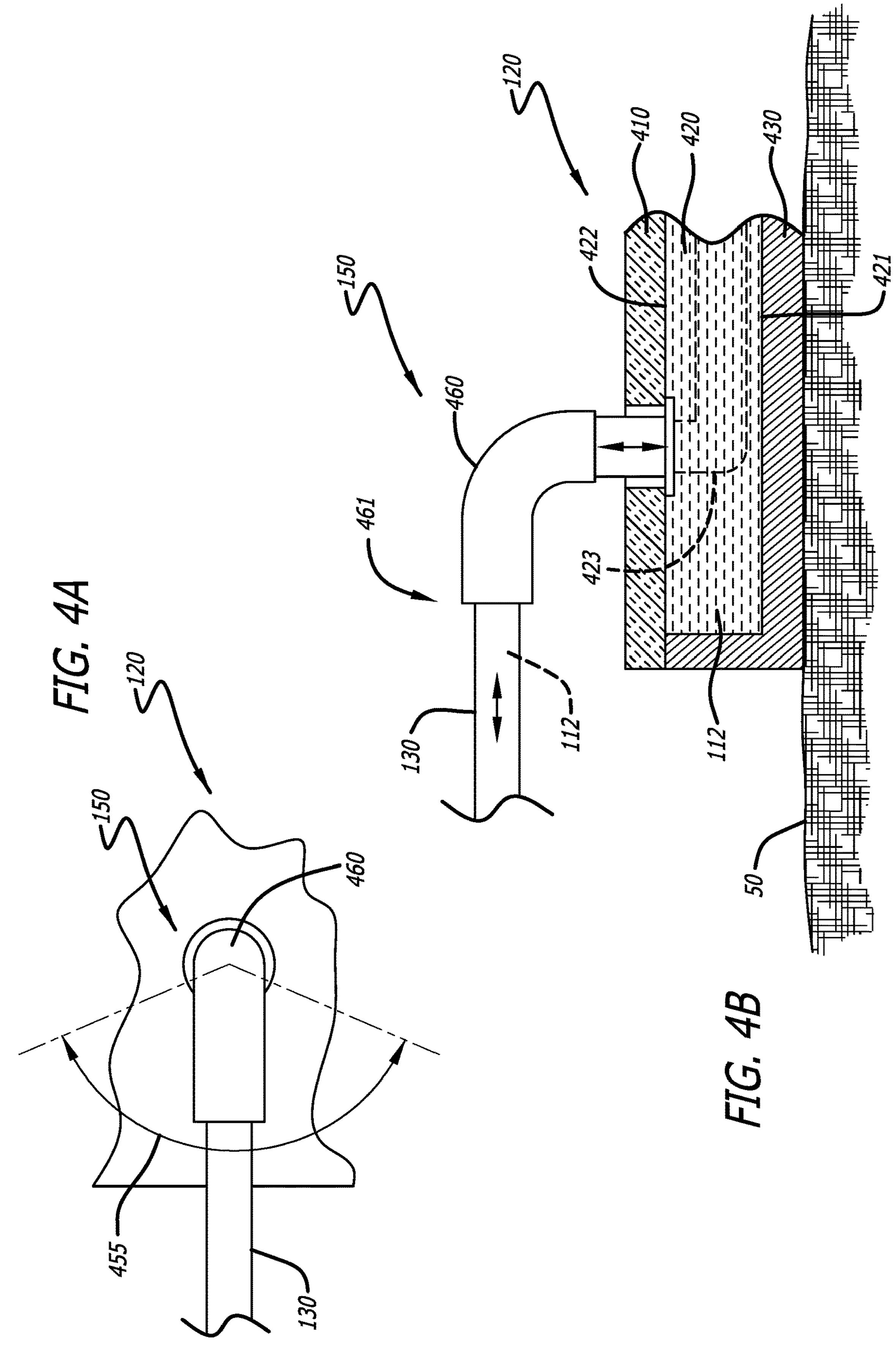
FIG. 4A is a top view of the portion the thermal contact pad of FIG. 1, in accordance with some embodiments.
FIG. 4B is a cross-sectional side view of the portion the thermal contact pad of FIG. 4A, in accordance with some embodiments.

FIG. 4A shows a top view of a portion of the thermal contact pad assembly 120 including the connector system 150 and the FDL 130 extending away from the connector system 150, in accordance with some embodiments. As illustrated, the connector system 150 may provide for a rotatable connection between the FDL 130 and the pad assembly 120. The rotatable connection may provide for the FDL 130 to rotate over an angle 455 ranging up to about 90 degrees, 180 degrees, or 360 degrees.

FIG. 4B shows a cross-sectional side view of a portion of the thermal contact pad assembly 120 in contact with the patient 50, in accordance with some embodiments. The pad assembly 120 may comprise multiple layers to provide multiple functions of the pad assembly 120. A fluid containing layer 420 is fluidly coupled to the FDL 130 via the connector system 150 to facilitate circulation of the TTM fluid 112 within the fluid containing layer 420. The fluid containing layer 420 having TTM fluid 112 circulating therein defines a heat sink or a heat source for the patient 50 in accordance with a temperature of the TTM fluid 112.

The pad assembly 120 may include a thermal conduction layer 430 disposed between the fluid containing layer 420 and the patient 50. The thermal conduction layer 430 is configured to facilitate thermal energy transfer between the fluid containing layer 420 and the patient 50. The thermal conduction layer 430 may be attached to the fluid containing layer 420 along a bottom surface 421 of the fluid containing layer 420. The thermal conduction layer 430 may be conformable to provide for intimate contact with the patient 50. In other words, thermal conduction layer 430 may conform to a contour of the patient 50 to facilitate thermal energy exchange between the thermal conduction layer 430 and the patient 50.

The pad assembly 120 includes an insulation layer 410 disposed on the top side of the fluid containing layer 420. The insulation layer 410 is configured to inhibit thermal energy transfer between the fluid containing layer 420 and the environment. The insulation layer 410 may be attached to the fluid containing layer 420 along a top surface 422 of the fluid containing layer 420. In some embodiments, the insulation layer 410 may comprise one or more openings 411 extending through the insulation layer 410 to provide for coupling of the FDL 130 with the fluid containing layer 420.

The connector system 150 may include an elbow 460 to change the direction of FDL 130 extending away from the connector system 150. As shown, the direction of FDL 130 is shifted from a direction perpendicular to the pad assembly 120 to a direction that is substantially parallel to the pad assembly 120. The elbow 460 also establishes an orientation of a distal portion 461 of the FDL 130 to be substantially parallel to the pad assembly 120 and/or the fluid containing layer 420. The fluid containing layer 420 may comprise one or more internal fluid conduits 426 fluidly coupled to the FDL 130 and the TTM fluid 112 may flow through the internal fluid conduits 426.

Figure 5A:
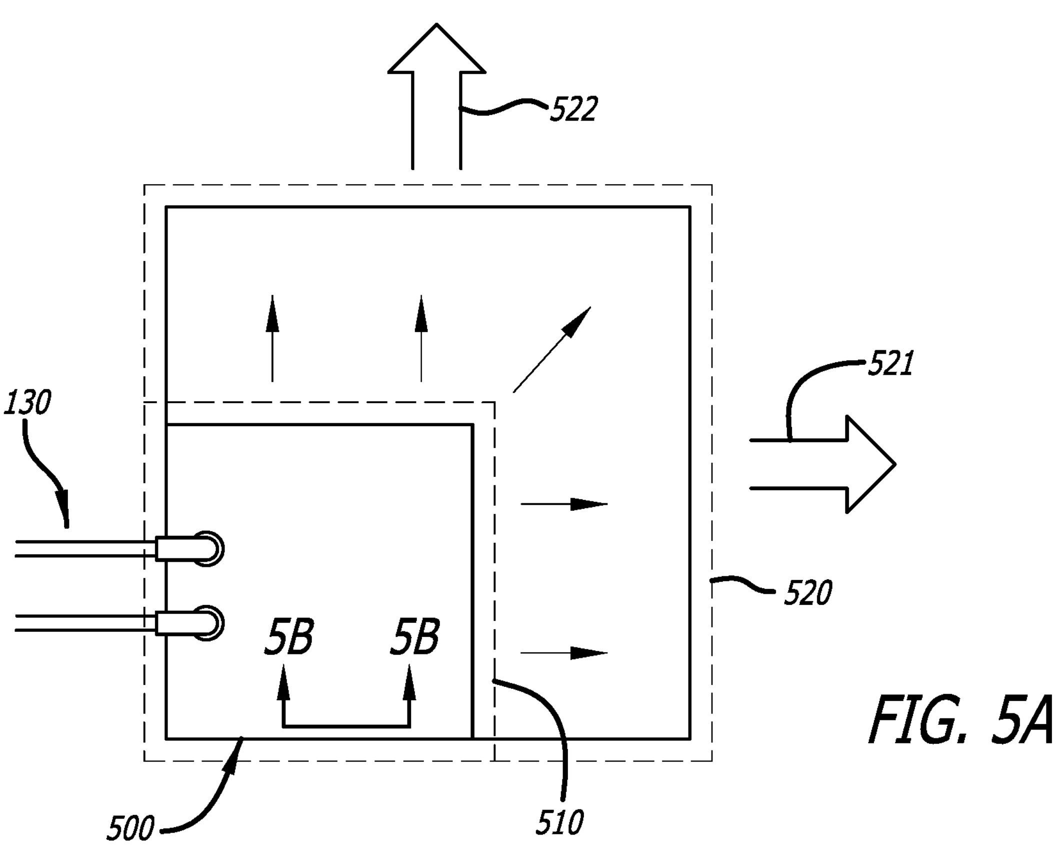
FIG. 5A is an illustration of an expandable thermal pad, in accordance with some embodiments.
Figure 5B:
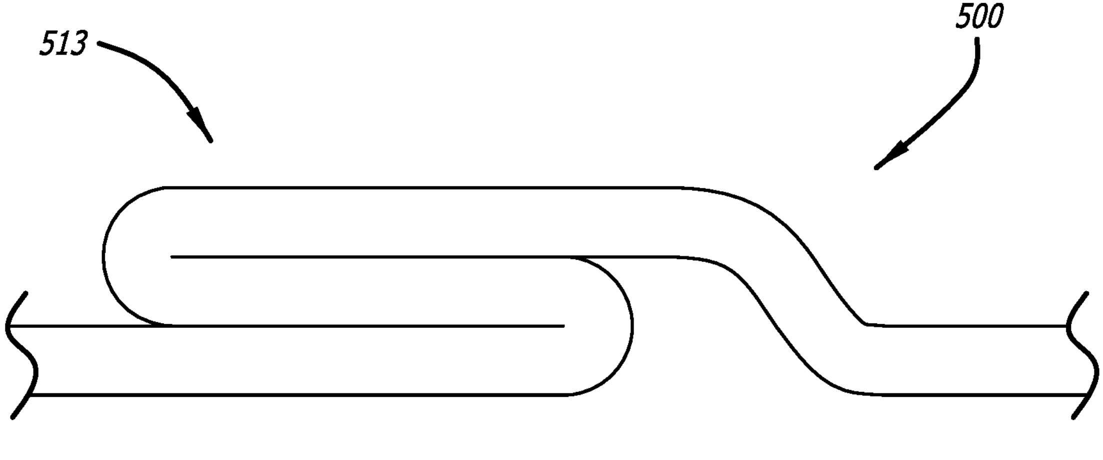
FIG. 5B is a cross-sectional view of a portion of the expandable thermal pad of FIG. 5A, in accordance with some embodiments.

FIGS. 5A and 5B illustrate an expandable pad 500 as may be comprised by the pad assembly 120, in accordance with some embodiments. FIG. 5A is a top view of the expandable pad 500 and FIG. 5B is a cross-sectional side view of a portion of the expandable pad 500 cut along sectioning lines 5B-5B. In the illustrated embodiment, the expandable pad 500 may be converted from a non-expanded state having a first patient contact area 510 to an expanded state having a second patient contact area 520. The second patient contact area 520 may be greater than the first patient contact area 510. The percentage of area increase with respect to the first patient contact area 510 may be up to about 10 percent, 25 percent, 50 percent, 100 percent or more.

In some embodiments, the expandable pad 500 may comprise a generally rectangular two-dimensional shape. In some embodiments, the expandable pad 500 may be expandable along a single dimension such as the length dimension 521 or the width dimension 522. In such an embodiment, the expandable pad 500 may be formed of materials that are generally non-stretchable. As shown in FIG. 5B, the expandable pad 500 may comprise one or more folds 513 defining overlapping portions of the expandable pad 500. As shown, the folds 513 may facilitate expansion expandable pad 500 along the length dimension 521. When in the non-expanded state, the first patient contact area 510 may include one or more overlapping area portions of the expandable pad 500. Expansion of the expandable pad 500 may comprise unfolding portions of the expandable pad 500 so that at least some of the overlapping area portions may be disposed in contact with the patient. In some embodiments, the expandable pad 500 may comprise folds 513 that facilitate expansion of the expandable pad 500 along the width dimension 522. In some embodiments, the pad 500 may comprise multiple folds 513 oriented in a substantially perpendicular direction with respect to the pad 500 defining a bellows arrangement of the overlapping area portions.

In some embodiments, the expandable pad 500 may be formed of materials that are generally stretchable. Stretchable materials may include elastomeric materials such as silicone, ethylene propylene diene monomer rubber (EPDM), rubber or any other suitably stretchable material. In some embodiments, the expandable pad 500 may be formed of, for example, a viscoelastic material. In some embodiments, the expandable pad 500 may be formed of any of a thermoplastic elastomer based on styrenic block copolymers, a thermoplastic urethane, a thermoplastic ester, a polyether block amide, and/or an olefin block copolymer. When formed of stretchable materials, the expandable pad 500 may be configured to expand along a single dimension (i.e., along the length 521 or the width 522) or along two dimensions such as along the length 521 and the width 522.

Figure 6A:
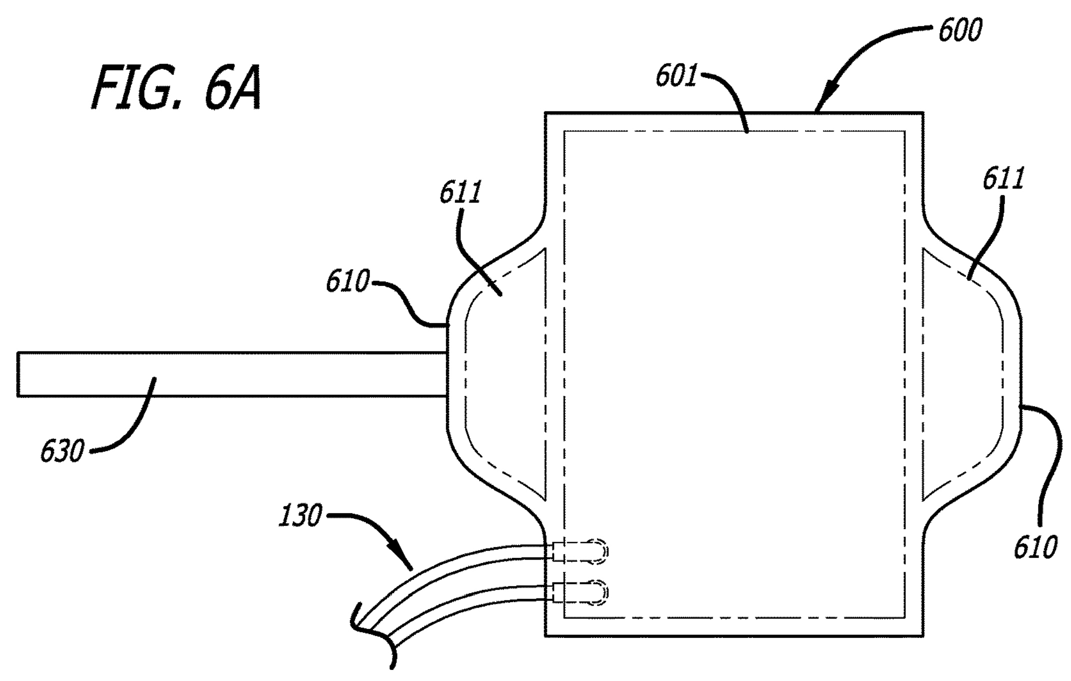
FIG. 6A is an illustration of a thermal pad that may be disposed between a patient and a surface of a bed, in accordance with some embodiments.
Figure 6B:
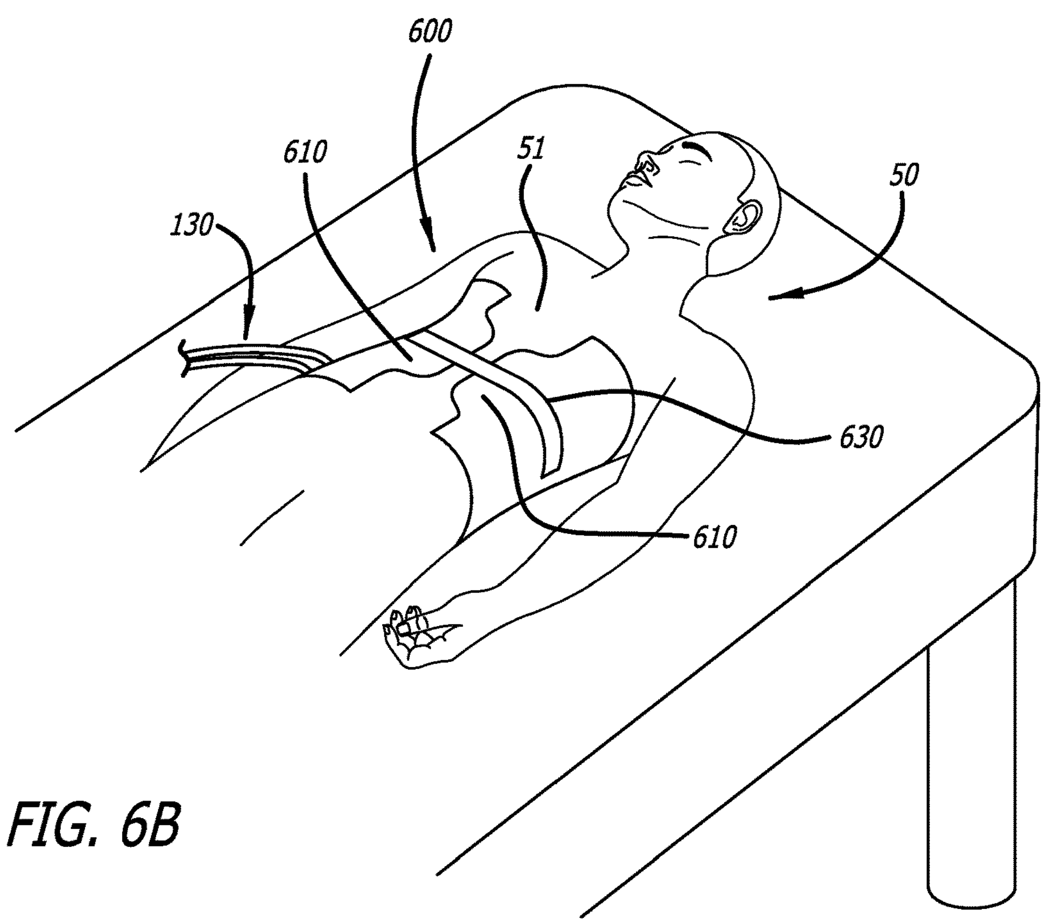
FIG. 6B is an illustration of a thermal pad of FIG. 6A wrapped around a torso of a patient, in accordance with some embodiments.

FIGS. 6A and 6B illustrate a thermal pad 600 as may be comprised by the pad assembly 120, in accordance with some embodiments. The thermal pad 600 may be configured to be disposed between the patient 50 and a bed surface. FIG. 6A shows a top view of the pad 600 and FIG. 6B shows the thermal pad 600 as may be applied to the patient 50. In the illustrated embodiment, the thermal pad 600 may be configured to establish a patient contact area 601 with the patient 50 when the patient 50 is laid on the thermal pad 600. In such an instance, a first patient contact area 601 may be defined by the portion of the thermal pad 600 that is disposed directly between the patient 50 and the bed surface.

The thermal pad 600 may comprise lateral extensions 610. The lateral extensions 610 may be configured to extend away from the patient along the bed surface. As such, in some instances, lateral patient contact areas 611 of the lateral extensions may be disposed away from (i.e., not in contact with) the patient 50. The lateral extensions 610 may also be configured to wrap around a portion of a torso 51 of the patient 50 so that the lateral patient contact areas 611 are in contact with the patient 50. In such an instance, a second patient contact area may be defined as the first patient contact are 610 combined with one or both of the lateral patient contact areas 611. In some embodiments, the thermal pad 600 may comprise one or more fastening members 630 (e.g., straps) configured to secure the lateral extensions 610 to the patient 50.

Figures 7A, 7B, 7C:
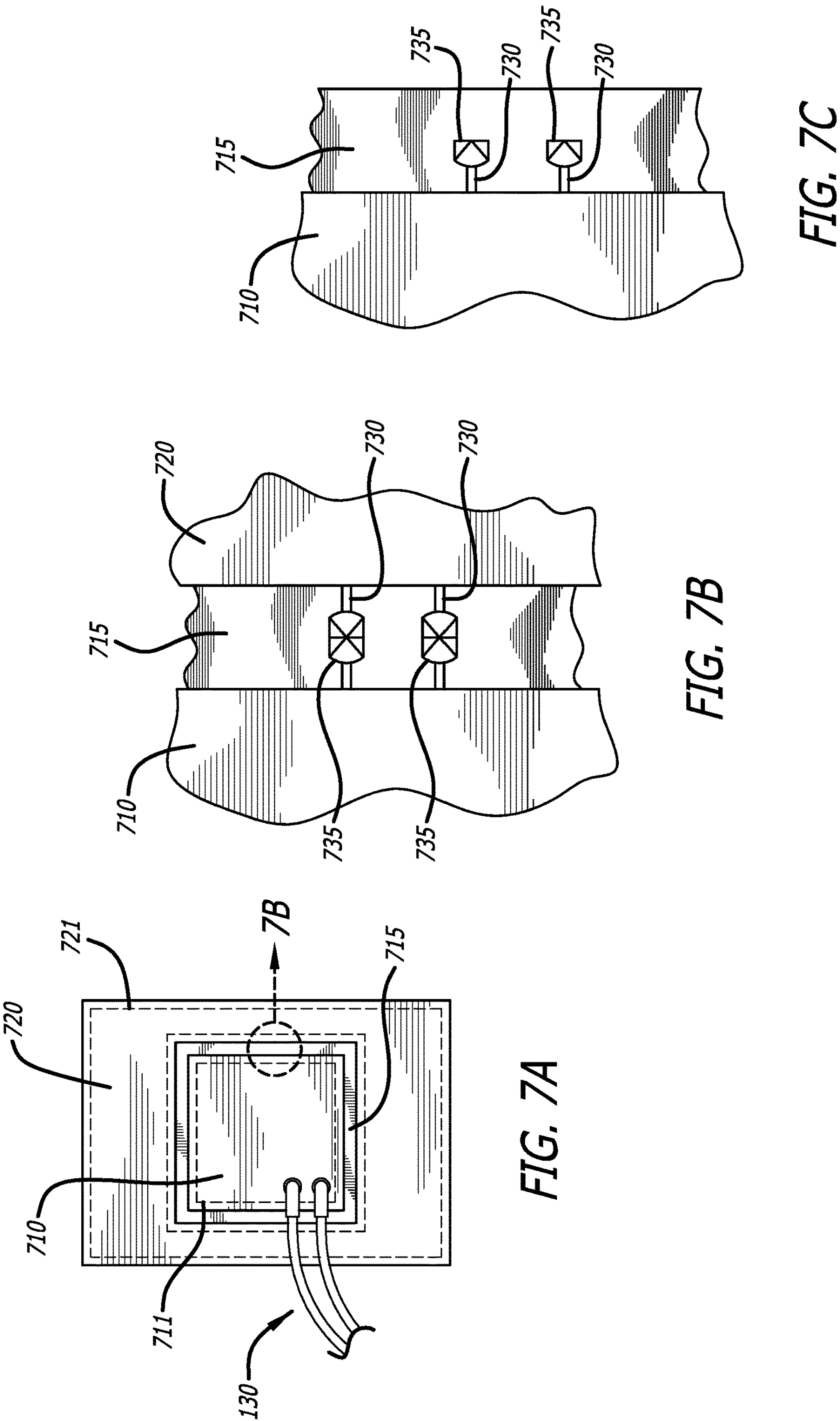
FIG. 7A is an illustration of a thermal pad comprising a removable portion, in accordance with some embodiments.
FIG. 7B is detail view of a portion thermal pad of FIG. 7A, in accordance with some embodiments.
FIG. 7C is detail view of a remaining portion of the thermal pad of FIG. 7A, in accordance with some embodiments.

FIGS. 7A-7C illustrate a thermal pad 700 as may be comprised by the pad assembly 120, in accordance with some embodiments. In use, a TTM therapy for a patient may be better facilitated by a thermal pad having a reduced patient contact area. The thermal pad 700 comprises a removable portion 720 coupled to a remaining portion 710. FIG. 7A is top view of the thermal pad 700. The removable portion 720 includes a patient contact area 721 and the remaining portion 710 includes a remaining patient contact area 711. The thermal pad 700 is convertible from a first patient contact area to a second patient contact area, wherein the first patient contact area comprises the removable patient contact area 721 combined with the remaining patient contact area 711, and the second patient contact area comprises only the remaining patient contact area 711.

A separation portion 715 is disposed between the removable portion 720 and the remaining portion 710. The separation portion 715 may comprise materials and/or structure to facilitate separation of the removable portion 720 from the remaining portion 710 by the clinician. In some embodiments, the separation portion 715 may include a perforation (not shown). In other embodiments, the removable portion 720 may be coupled to the remaining portion 710 via 1, 2, 3, 4, or more discreet connecting elements (not shown) extending between the remaining portion 710 and the removable portion 720. In some embodiments, the separation portion 715 may facilitate separation of the removable portion 720 from the remaining portion 710 via the use of a tool by the clinician such as a knife or scissors. In some embodiments, the FDL 130 may be connected to the remaining portion 710.

FIG. 7B is a detail view of a portion of the thermal pad 700 showing one or more fluid conduits 730 extending across the separation portion 715. The fluid conduits 730 may provide for flow of TTM fluid 112 between the removable portion 720 from the remaining portion 710. Each of the fluid conduits 730 may include one or more occlusion mechanisms 735 (e.g., a valves) configured for occlusion of the fluid conduits 730 of the upon removal of the removable portion 720. The occlusion mechanism 735 may be disposed in an open state (i.e., allowing flow through the fluid conduit 730) when the removable portion 720 is coupled to the remaining portion 710, and the occlusion mechanism 735 may be disposed in a closed state (i.e., occluding the fluid conduit 730) when the removable portion 720 is decoupled from the remaining portion 710. FIG. 7C is a detail view of a portion of the pad 700 showing the one or more fluid conduits 730 extending away from the remaining portion 710 after separation of the removable portion 720. The remaining portion 710 may include the occlusion mechanisms 735 to seal the open ends of the fluid conduits 730. In some embodiments, the occlusion mechanism 735 may comprise a clamp configure to clamp off the fluid conduit 730. In other embodiments, the occlusion mechanism 735 may comprise a plug configured for insertion within the fluid conduits 730 thereby sealing the open end. Other mechanisms, devices, and methods suitable for occluding the open end of each fluid conduit 730, as may be considered by one of ordinary skill, are included in this disclosure.

As illustrated in FIG. 7A, the removable portion 720 may be coupled to the remaining portion 710 along an entire circumference of the remaining portion 710. In other embodiments, the removable portion 720 may be coupled to the remaining portion 710 along a partial perimeter of the remaining portion 710. In some embodiments, the thermal pad 700 may include more than one removable portion 720 and in such embodiments, one removable portion may be coupled to another removable portion.

Figures 8A, 8B:
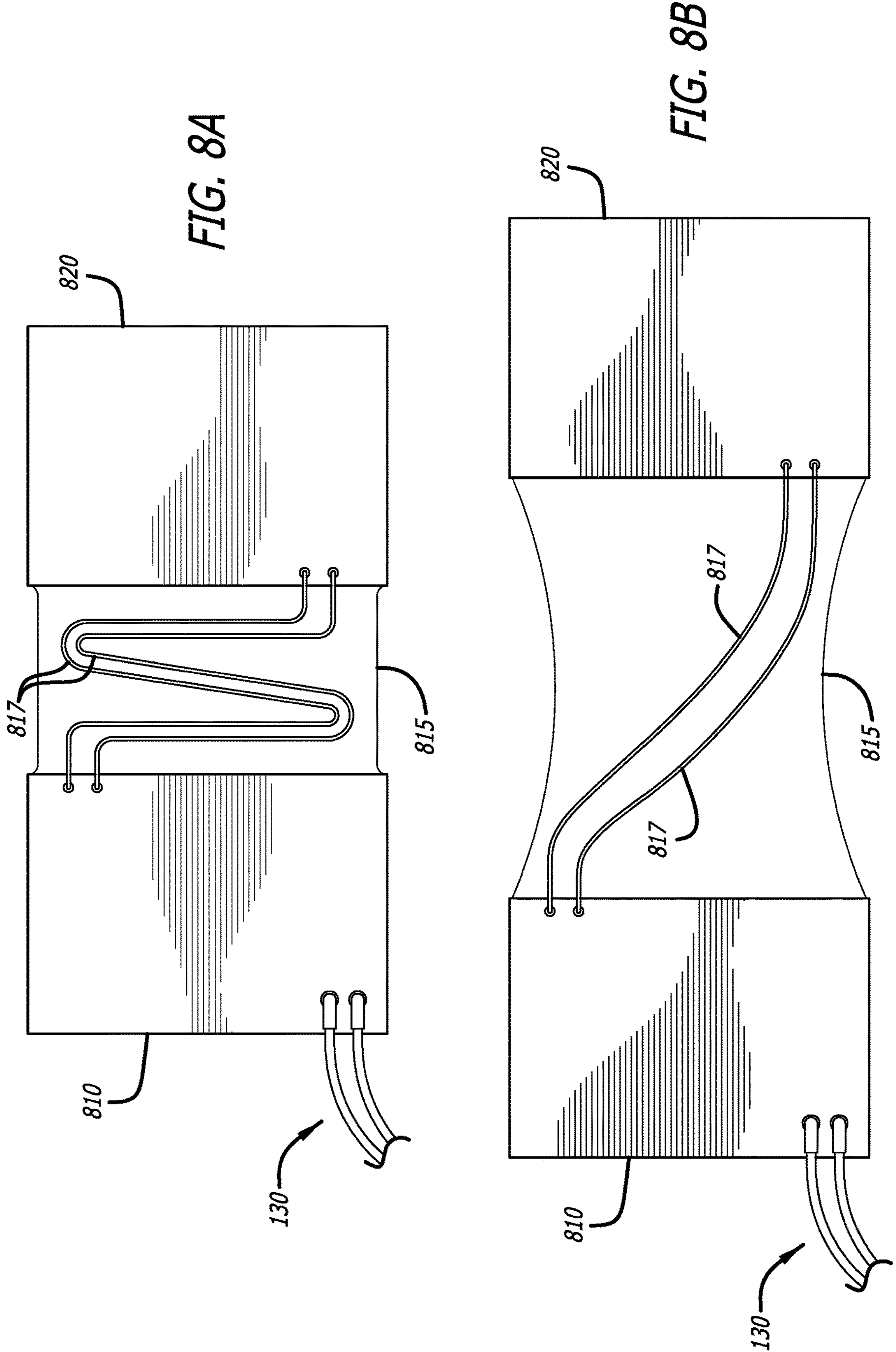
FIG. 8A is an illustration of thermal pad comprising an extendable portion in a non-extended state, in accordance with some embodiments.
FIG. 8B is an illustration of the thermal pad of FIG. 8A with the extendable portion in an extended state, in accordance with some embodiments.

FIGS. 8A and 8B illustrate a thermal pad 800 as may be comprised by the pad assembly 120, in accordance with some embodiments. In some instances, a TTM therapy may be better facilitated by performing thermal energy exchange at separate locations of the patient such as on the front side of the torso and the back side of the torso. The thermal pad 800 comprises a first pad portion 810, a second pad portion, and an extendable member 815 disposed between the first pad portion 810 and the second pad portion 820. FIG. 8A shows the pad 800 in a contracted state and FIG. 8B shows the pad 800 in an extended state.

The extendable member 815 may comprise one or more fluid conduits 817 extending between the first portion 810 and the second portion 820. The fluid conduits 817 may provide for flow of TTM fluid 112 between the first portion 810 and the second portion 820. The extendable member 815 may be formed of a stretchable material such as a stretchable fabric. In other embodiments, the first portion 810, second portion 820, and the extendable member 815 may be formed of the same materials. In some embodiments, the fluid conduits 817 may comprise a serpentine path across the extendable member 815.

Figure 9A:
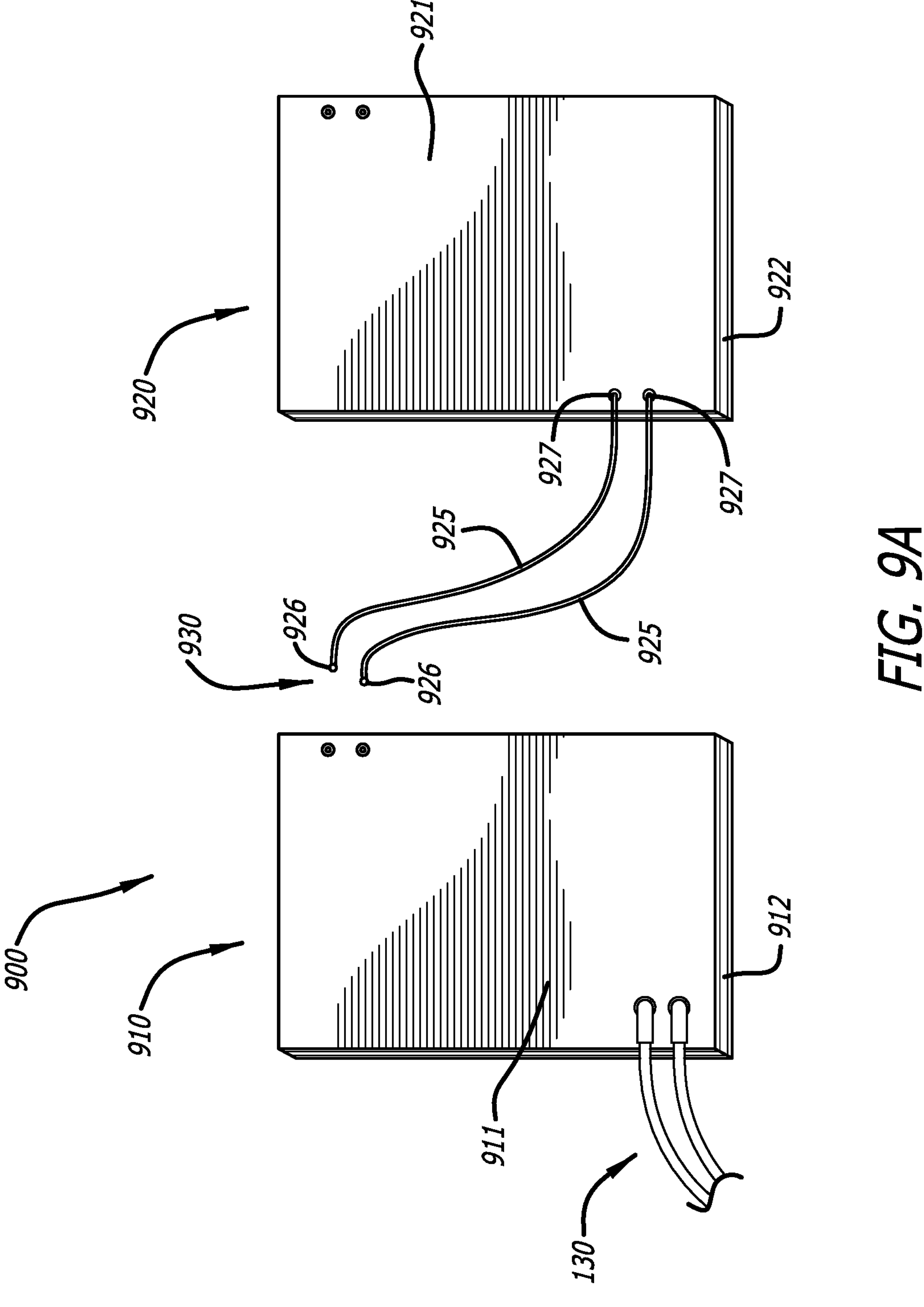
FIG. 9A is an illustration of a thermal pad system comprising a first pad fluidly connectable to a second pad, in accordance with some embodiments.

FIG. 9A is an illustration of a thermal pad system 900 as may be comprised by the pad assembly 120, in accordance with some embodiments. In some instances, a TTM therapy may be better facilitated by adding a second thermal pad to a first pad to increase the patient contact area. The thermal pad system 900 include a first pad 910 and a second pad 920 coupleable to the first pad 910 in a daisy chain arrangement. The first pad 910 comprises a first fluid containing layer 912 and a first patient contact area 911, and the second pad 920 comprises a second fluid containing layer 922 and a second patient contact area 921. In use, the clinician may connect to the first pad 910 to increase the patient contract area. As such, the first patient contact area 911 of the thermal pad 900 may be combined with the second patient contact area 921 to define a combined patient contact area.

The thermal pad 900 may comprise one or more fluid conduits 925 extending between the first pad 910 and the second pad 920. The fluid conduits 925 may provide for flow of TTM fluid 112 between the first fluid containing layer 912 of the first pad 910 and the second fluid containing layer 922 of the second pad 920. In use, the clinician may attach and fluidly couple the second pad 920 to the first pad 910. The fluid conduits 925 may be attached and fluidly coupled to the second pad 920 at a second end 927 of the fluid conduits 925. Similarly, the fluid conduits 925 may be attachable and fluidly coupleable to the first pad 910 at a first end 926 of the fluid conduits 925.

Figures 9B, 9C:
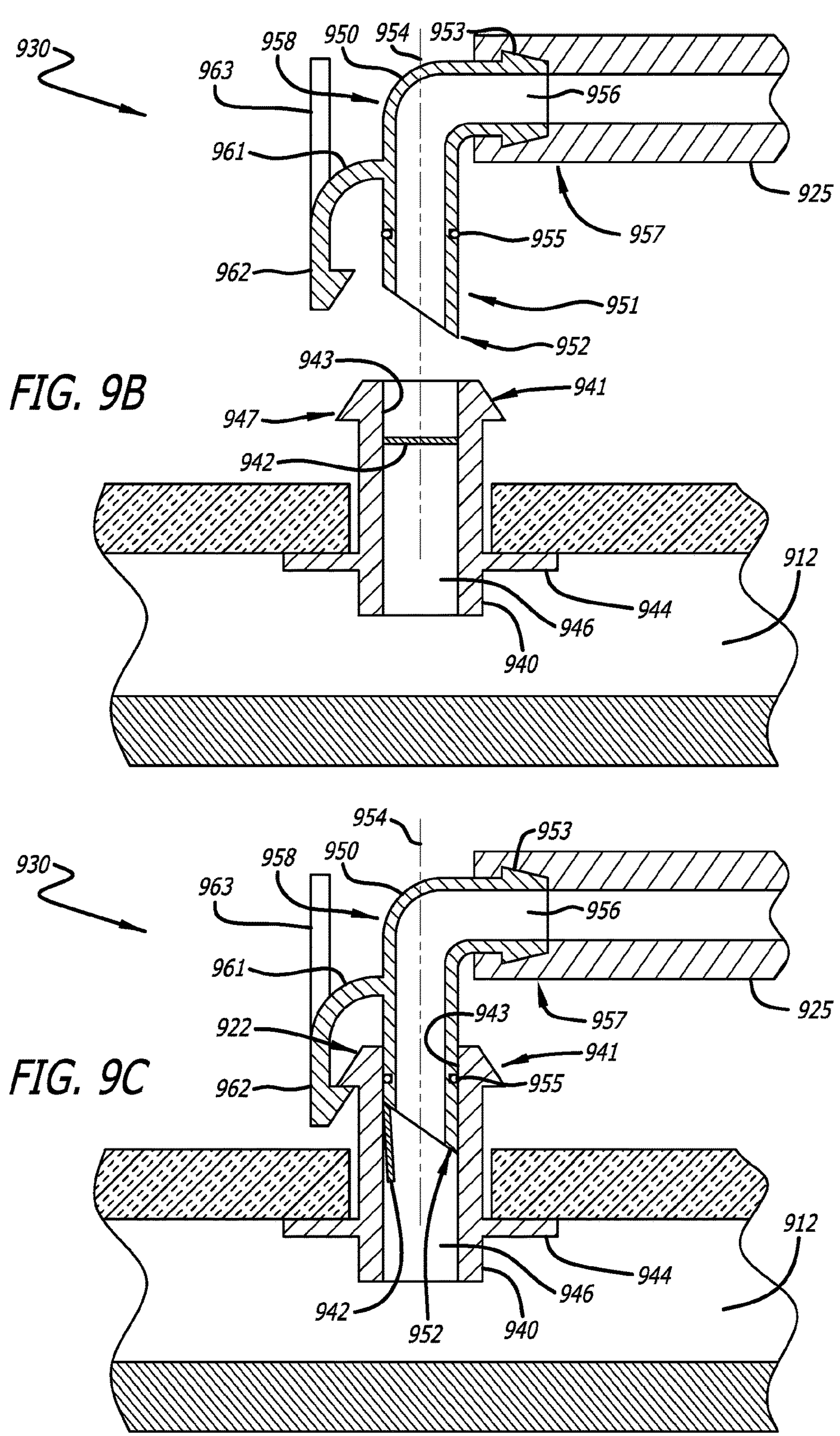
FIG. 9B is an illustration of a connector set of the thermal pad system of FIG. 9A, where the connector set is disposed in a disconnected state, in accordance with some embodiments.
FIG. 9C is an illustration of the connector set of FIG. 9B disposed in a connected state, in accordance with some embodiments.

FIGS. 9B and 9C illustrate a connector set connector set 930 that may be included with thermal pad system 900 for connecting the second pad 920 to the first pad 910. FIG. 9B shows an exploded cross-sectional side view of the connector set 930 including a pad connector 940 and a complementary fluid line connector 950. FIG. 9C shows an assembled cross-sectional side view of the connector set 930. The fluid line connector 950 is attached to the fluid conduit 925 and the pad connector 640 is attached to a fluid containing layer 912 of the first pad 910. The fluid line connector 950 and the pad connector 940 establish fluid communication between the fluid conduit 925 and the fluid containing layer 912. The connectors 940, 950 are configured to sealably couple together to establish fluid communication between a lumen 956 of the fluid line connector 950 and a lumen 946 of the pad connector 940. The fluid line connector 950 comprises a post portion 951 and the pad connector 940 comprises a post receiving portion 941.

The post portion 951 and the post receiving portion 941 are sized and shaped to form a seal between the pad connector 940 and a fluid line connector 950. The fluid line connector 950 may comprise a sealing member 955 (e.g., an O-ring) to the establish the seal. The pad connector 940 comprises an annular sealing surface 943 to sealably engage the sealing member 955. In some embodiments, the pad connector 940 may comprise the sealing member 955 and the fluid line connector 950 may comprise the annular sealing surface 943. In some embodiments, the post portion 951 may be formed to provide a seal directly with the annular sealing surface 9433. In such embodiments, the sealing member 955 may be omitted.

The post portion 951 and the post receiving portion 941 are sized to provide a sliding fit between the pad connector 940 and a fluid line connector 950. The sliding fit may provide for insertion of the post portion 951 within the post receiving portion 941 and may also provide for rotation of the fluid line connector 950 about the axis 954 with respect to the pad connector 940. In other words, the sliding fit may provide for a rotatable connection between the pad connector 940 and the fluid line connector 950. The fluid line connector 950 may comprise an elbow 958 of about 90 degrees so that a fluid line coupling portion 957 extends in a substantially perpendicular direction away from the axis 654.

In some embodiments, the pad connector 940 may comprise a septum 942 extending across the lumen 946 and forming a seal across the lumen 946. In some embodiments, the post portion 951 may comprise a spike 952 configured to rupture the septum 942 when the fluid line connector 950 is coupled to the pad connector 940 as shown in FIG. 9C. In use the septum 942 may function as a valve, where the valve is closed with the septum 942 is intact and the valve is open when the septum 942 is ruptured. In some embodiments, the septum 942 and the spike 952 may be omitted. In some embodiments, the pad connector 940 may include a valve (not shown) that may be selectively opened and/or closed by the clinician.

The pad connector 940 may comprise a flange 944 to facilitate coupling of the pad connector 940 with the fluid containing layer 912 of the first pad 910. The flange 944 may be coupled to the fluid continuing layer 912 via radio frequency welding, ultrasonic welding, adhesive bonding or any suitable coupling process. The fluid line coupling portion 957 may comprise a barb 953 for coupling the fluid line connector 950 to the fluid conduit 925. Alternatively, the fluid line coupling portion 957 may comprise a bonding socket or any other suitable feature for coupling the fluid line connector 950 to the fluid conduit 925.

The connectors 950, 940 may be configured to couple together via a snap fit. In an exemplary embodiment, the snap fit may comprise one or multiple hooks 962 of the fluid line connector 950 configured to engage with an annular ridge 947 of pad connector 940. The hook 962 may comprise a flexible portion 961 to allow for deflection of the hook 962 upon engagement with the annular ridge 947. The snap fit may be configured to facilitate coupling of the connectors 950, 940 via longitudinal displacement fluid line connector 950 with respect to the pad connector 940. In some embodiments, the snap fit may comprise a release mechanism such as the lever arm 963. Operation of the lever arm 963 may disengage the hook 962 from the annular ridge 962 allowing separation of the fluid line connector 950 from the pad connector 940.

Each of the fluid conduits 925 may comprise a fluid line connector 950 at the first end 926. Similarly, the first pad 910 may comprise one or more corresponding pad connectors 940. In use, the clinician may connect each fluid line connector 950 to the corresponding pad connector 940 to attach and fluidly couple the second pad 920 to the first pad 910. During connection, the clinician may rupture the septum 942 (i.e., open the valve) of each pad connector 940.

In some embodiments, the thermal pad system 900 may include additional thermal pads coupled to each other in the daisy chain arrangement described above. The thermal pad system 900 may include 2, 3, 4, 5, 6, or more thermal pads.

Figure 10A:
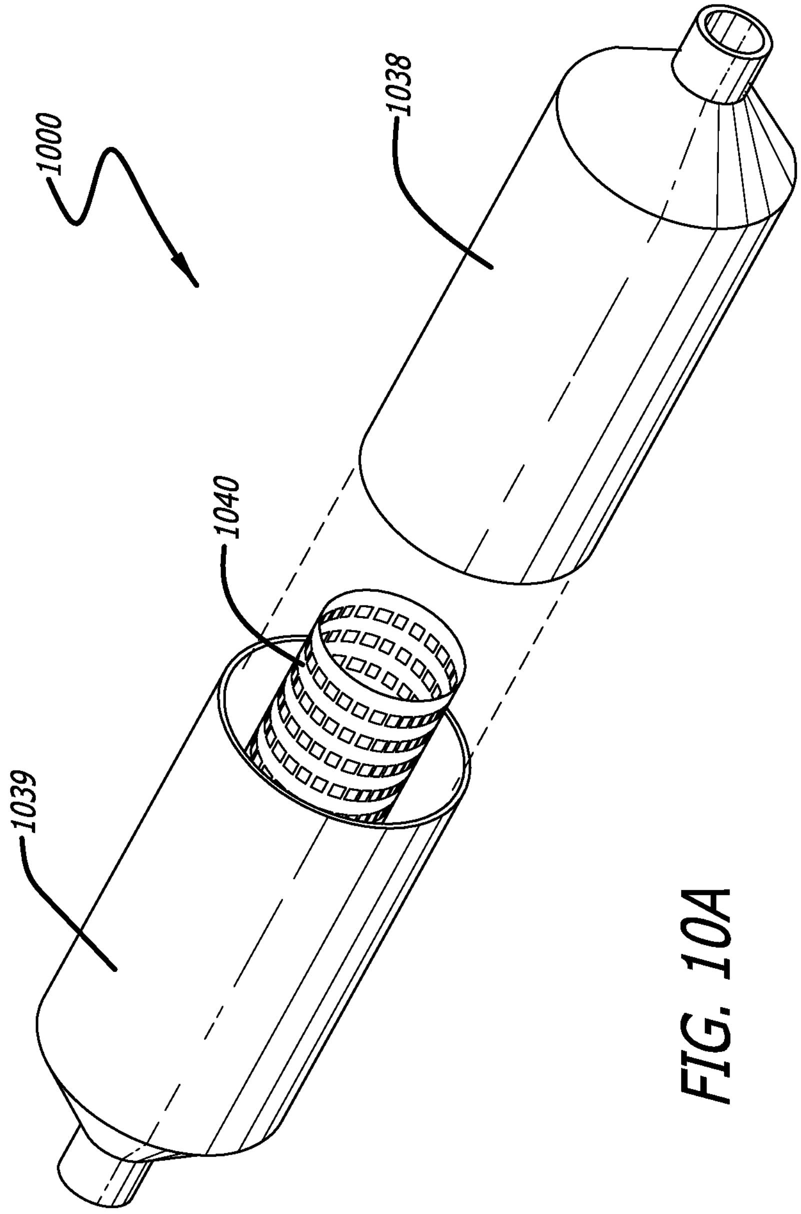
FIG. 10A provides an exploded perspective view of a TTM fluid filter, in accordance with some embodiments.
Figure 10B:
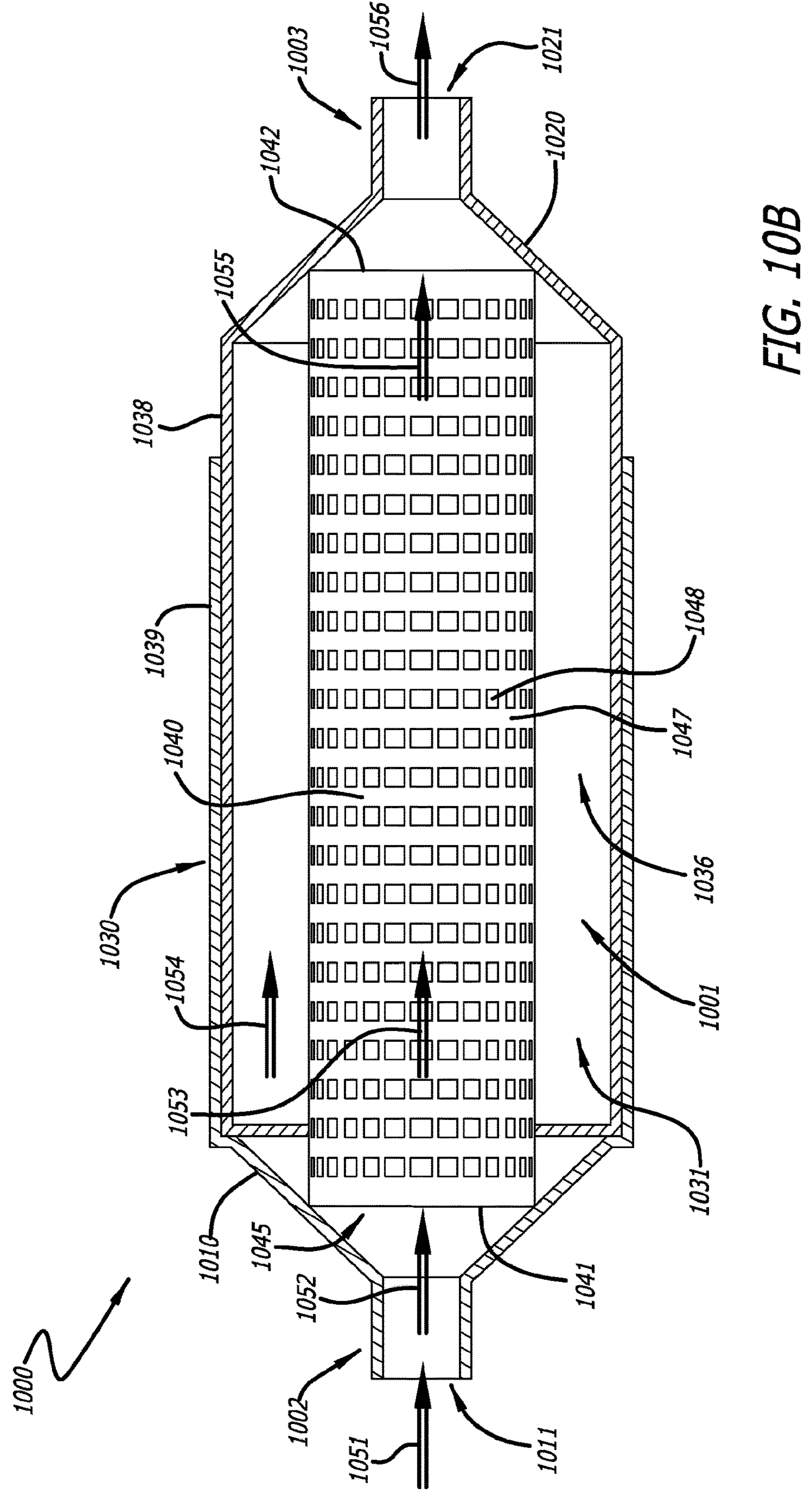
FIG. 10B provides a cross-sectional side view of the filter of FIG. 10A, in accordance with some embodiments.

FIGS. 10A and 10B show a filter 1000 that may be included with the TTM system 100. The filter 1000 may be disposed in line with a TTM fluid flow path of the TTM system 100 so that the circulating TTM fluid 112 flows through the filter 1000. The filter 1000 may be configured to remove (i.e., filter out) material/particles having a size of 0.2 microns or larger from the TTM fluid 112 without causing a flow restriction of the TTM fluid 112.

The filter 1000 comprises a longitudinal shape having a flow path 1001 extending from a first end 1002 to a second end 1003. The filter 1000 comprises a diffuser 1010 adjacent the first end 1002, a nozzle adjacent 1020 the second end 1003, and a body 1030 extending between the diffuser 1010 and the nozzle 1020. Along the diffuser 1010, a cross-sectional flow area of the filter 1000 expands from an inlet flow area 1011 to a body flow area 1031 and along the nozzle 1020, the cross-sectional flow area of the filter 1000 contracts from the body flow area 1031 to an outlet flow area 1021. In some embodiments, the inlet flow area 1011 and the outlet flow area 1021 may be substantially equal.

In some embodiments, the body flow area 1031 may be constant along the body 1030. In other embodiments, the body flow area 1031 may vary along a length of the body 1030 such that the body flow area 1031 is greater or less along middle portion of the body 1030 than at the ends of the body 1030. In some embodiments, the body flow area 1031 may be circular.

The filter 1000 comprises an inner tube 1040 disposed within the body 1030 extending along the length of body 1030. The inner tube 1040 may be coupled to the diffuser 1010 at a first inner tube end 1041 so that TTM fluid 112 entering the filter 1000 at the first end 1002 also enters the inner tube 1040 at the first inner tube end 1041. The inner tube 1040 may be coupled to the nozzle 1020 at a second inner tube end 1042 so that TTM fluid 112 exiting the filter 1000 at the second end 1003 also exits the inner tube 1040 at the second inner tube end 1042.

The inner tube 1040 comprises an inner tube flow area 1045 extending the length of the inner tube 1040. The inner tube flow area 1045 may be greater than the inlet flow area 1011 and/or the outlet flow area 1021. The inner tube flow area 1045 may be constant along the length of the inner tube 1040. In some embodiments, the inner tube flow area 1045 may vary along the length of the inner tube 1040. In some embodiments, the inner tube 1040 may comprise a circular cross section. The inner tube 1040 and the body 1030 may be configured so that the body flow area 1031 comprises a combination of the inner tube flow area 1045 and an annular flow area 1036.

The inner tube 1040 comprises a porous a circumferential wall 1047. The porous wall 1047 may be configured so that TTM fluid 112 may flow through the porous wall 1047, i.e., through the pores 1048 of the porous wall 1047. Consequently, TTM fluid 112 may flow through the porous wall 1047 from the inner tube flow area 1045 to the annular flow area 1036 and from the annular flow area 1036 into the inner tube flow area 1045.

In use, the longitudinal velocity of the TTM fluid 112 may change along the length of the filter 1000. As the volumetric TTM fluid 112 flow through the filter is constant, the longitudinal velocity of the TTM fluid 112 may be at least partially defined by the flow areas of the filter 1000 as described below. The TTM fluid 112 may enter the filter 1000 at a first longitudinal velocity 1051 and decrease along the diffuser so that the TTM fluid 112 enters the inner tube at a second velocity 1052 less than the first longitudinal velocity 1051. At this point, a portion of the TTM fluid 112 may flow through the porous wall 1047 from the inner tube flow area 1045 into the annular flow area 1036 to divide the fluid flow into a third velocity 1053 within the inner tube flow area 1045 and a fourth velocity 1054 within the annular flow area 1036. The fourth velocity 1054 may be less than the third velocity 1053. A portion of the TTM fluid 112 may then flow back into the inner tube flow area 1045 from the annular flow area 1036 to define a fifth velocity 1055 along the inner tube flow area 1045 which may be about equal to the second velocity 1052. The TTM fluid 112 may then proceed along the nozzle 1020 to define a sixth velocity 1056 exiting the filter 1000. In some embodiments, the first velocity 1051 and the sixth velocity 1056 may be about equal.

The filter 1000 may be configured to remove harmful bacteria and viruses from the TTM fluid 112 using sedimentation principles. In use, the filter 1000 may be oriented horizontally so that the direction of fluid flow through the filter 1000 is perpendicular to a gravitational force 1065. In some instances, bacteria, viruses, and other particles within the TTM fluid 112 may have a greater density than the TTM fluid 112 and as such may be urged by the gravitational force 1065 (i.e., sink) in a direction perpendicular to the fluid flow direction. In some instances, particles within the inner tube flow area 1045 may sink toward and through the porous wall 1047 into the annular flow area 1036. Particles within the annular flow area 1036 may then sink toward an inside surface 1031 of the body 1030 and become trapped adjacent the inside surface 1031. The geometry of the filter 1000 may be configured to allow 0.2-micron bacteria/virus particles to fall out of the flow of TTM fluid 112 and become trapped along the inside surface 831.

In some embodiments, the filter 1000 may be configured so that flow of TTM fluid 112 from the inner tube flow area 1045 into the annual flow area 1036 may drag particles through the porous wall 1047. In some embodiments, the inlet flow area 1011, the inner tube flow area 1045, and the annual flow area 1036 may be sized so that the third velocity 1053 is less than about 50 percent, 25 percent, or 10 percent of the first velocity 1051 or less. In some embodiments, the body 1030 and the inner tube 1040 may be configured so that the fourth velocity 1054 is less than the third velocity 1053. In some embodiments, the fourth velocity 1054 may less than about 50 percent, 25 percent, or 10 percent of the third velocity 1053 or less.

In some embodiments, the filter 1000 may be configured so that the flow within the inner tube flow area 1045 is laminar flow, i.e., so that the velocity of the fluid flow adjacent to or in close proximity to an inside surface 1041 of the porous wall 1047 is less than the velocity at a location spaced away from the inside surface 1041. In such an embodiment, the particles may more readily sink toward and through the porous wall 1047.

In some embodiments, the filter 1000 may be configured so that the fluid flow within the annual flow area 1036 is laminar flow, i.e., so that the velocity of the fluid flow adjacent to or in close proximity to inside surface 1031 of the body 1030 is less than the velocity at a location spaced away from the inside surface 1031. In such an embodiment, the particles may more readily sink toward and be trapped along the inside surface 1031.

The filter 1000 may comprise three components including the inner tube 1040 an inner body shell 1038, and an outer body shell 1039. Each of the three components may be formed via the plastic injection molding process. Assembly of the filter 1000 may include capturing the inner tube 1040 within the inner body shell 1038 and the outer body shell 1039 and sliding the inner body shell 1038 into the outer body shell 1039 wherein the fit between the inner body shell 1038 and the outer body shell 1039 is an interference fit.

Figure 10C:
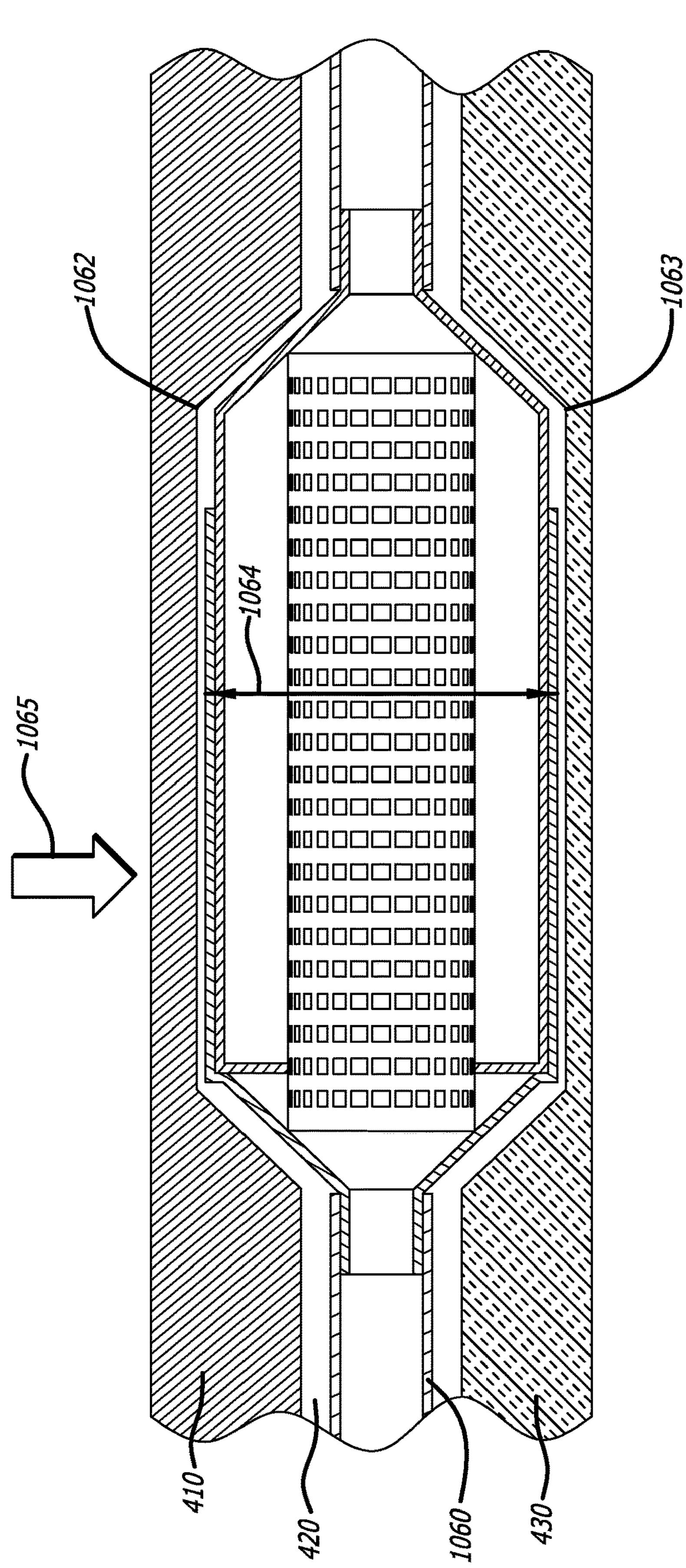
FIG. 10C provides a side cross-sectional view of the thermal contact pad of FIG. 1 incorporating the filter of FIG. 10A, in accordance with some embodiments.

In some embodiments, the filter 1000 may be disposed within the pad assembly 120. FIG. 10C shows a detail cross-sectional view of the pad assembly 120 including the filter 1000 disposed within the fluid containing layer 420. The filter 1000 is coupled in line with an internal flow path 1060 within the fluid containing layer 420 so that TTM fluid 12 circulating within the pad assembly 120 passes through the filter 1000. The filter 1000 may be sized so that the inlet flow area 1011 and the outlet flow area 1021 are similar to a cross-sectional flow area of the internal flow path 1060 within the fluid containing layer 420.

In some embodiments, a thickness of the fluid containing layer 420 may increase adjacent the filter 1000 to accommodate a body diameter 1064 of the filter 1000. To further accommodate the body diameter 1064, the insulation layer 410 and/or the thermal conduction layer 430 may comprise internal depressions 1062, 1063, respectively.

In some embodiments, one or more filters 1000 may be disposed in line with the flow of TTM fluid 112 at other locations of the TTM system 100. In some embodiments, one or more filters 1000 may be disposed within the TTM module 110. In some embodiments, one or more filters 1000 may be disposed in line with the FDL 130. In some embodiments, the filter 1000 may be disposed in line with a fluid conduit of the pad external to the fluid containing layer 420 such as a conduit extending between the pad connector 652 and the pad assembly 120.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. A medical pad for exchanging thermal energy between a targeted temperature management (TTM) fluid and a patient, the medical pad comprising:

a fluid containing layer for containing the TTM fluid, the fluid containing layer configured for circulating the TTM fluid within the fluid containing layer; and a patient contact surface defining a patient contact area to facilitate thermal energy exchange with the patient, wherein:

the patient contact area is convertible from a first patient contact area to a second patient contact area, the second patient contact area is different from the first patient contact area, the first patient contact area is converted to the second patient contact area when a removable portion having the patient contact area of the medical pad is separated from a remaining portion of the medical pad, the removable portion comprises a removable fluid containing layer, the remaining portion comprises a remaining fluid containing layer, and the medical pad comprises one or more fluid conduits extending between the remaining fluid containing layer and the removable fluid containing layer.

2. The medical pad of claim 1, wherein the second patient contact area is at least 10 percent greater than the first patient contact area.

3. The medical pad of claim 2, wherein the patient contact area is expandable from the first patient contact area to the second patient contact area.

4. The medical pad of claim 3, wherein the patient contact area is expandable along a single dimension.

5. The medical pad of claim 3, wherein the medical pad comprises one or more folds to facilitate expansion from the first patient contact area to the second patient contact area.

6. The medical pad of any of claim 3, wherein the medical pad comprises a stretchable material to facilitate expansion from the first patient contact area to the second patient contact area.

7. The medical pad of claim 1, wherein the medical pad comprises:

a first pad defining the first patient contact area; and a second pad connectable to the first pad, the second pad including a separate second patient contact area, wherein when the first patient contact area is converted to the second patient contact area, the second pad is connected to the first pad thereby combining the first patient contact area with the separate second patient contact area to define the second patient contact area.

8. The medical pad of claim 7, wherein:

the first pad includes a first fluid containing layer, the second pad includes a second fluid containing layer, and when the second pad is connected to the first pad, the second fluid containing layer is fluidly coupled to the first fluid containing layer so that the TTM fluid is circulatable within the second fluid containing layer.

9. The medical pad of claim 8, wherein:

the first pad includes at least one first connector including a valve;

the second pad includes at least one second connector, and when the second pad is connected to the first pad, the at least one first connector is coupled to the at least one second connector and the valve of the at least one first connector is transitioned from a closed state to an opened state.

10. The medical pad of claim 1, wherein the removable portion is disposed along an entire circumference of the remaining portion.

11. The medical pad of claim 1, wherein each of the one or more fluid conduits comprises a valve, and wherein when the first patient contact area is converted to the second patient contact area a removable portion of the one or more fluid conduits is separated from a remaining portion of the one or more fluid conduits, the remaining portion comprising the valve, and the valve is closed.

12. The medical pad of claim 1, wherein the medical pad is configured to be disposed on a bed surface, and wherein the first contact area is defined by a portion of the medical pad disposed between the patient and the bed surface.

13. The medical pad of claim 12, wherein the medical pad comprises one or more lateral extensions extending away from the patient along the bed surface, and wherein when the first patient contact area is converted to the second patient contact area at least a portion of the one or more lateral extensions is wrapped around a portion of the patient to define the second patient contact area.

14. The medical pad of claim 13, wherein the portion of the patient comprises at least a portion of a torso of the patient.

15. The medical pad of claim 13, wherein the medical pad comprises one or more straps to secure the one or more lateral extensions around the portion of the patient.

16. The medical pad of claim 1, wherein a first portion of the medical pad comprising a first portion of the patient contact area is separable from a second portion of the medical pad comprising a second portion of the patient contact area, and wherein the first portion of the medical pad is coupled to the second portion of the medical pad via an extendable member, the extendable member including a stretchable material.

17. The medical pad of claim 16, wherein the extendable member comprises one or more fluid conduits extending between the first portion of the medical pad and the second portion of the medical pad.

18. The medical pad of claim 1, wherein the fluid containing layer comprises a TTM fluid flow path, and wherein the medical pad further comprises a filter disposed in line with the TTM fluid flow path.

19. A method of providing a targeted temperature management (TTM) therapy to a patient, comprising:

providing a TTM system comprising:

a TTM module configured to provide a TTM fluid;

a first thermal pad comprising:

a fluid containing layer configured to receive the TTM fluid from the TTM module to facilitate thermal energy transfer between the TTM fluid and a patient; and a thermal conduction layer disposed on a bottom surface of the fluid containing layer; and a fold extending along a length of the first thermal pad, wherein:

the fold defines a first portion of the first thermal pad and a second portion of the first thermal pad overlapping the first portion of the first thermal pad, and the first portion and the second portion face a same direction; and a fluid delivery line (FDL) extending between the TTM module and the first thermal pad, the FDL configured to provide TTM fluid flow between the TTM module and the first thermal pad, wherein:

the first thermal pad further comprises a patient contact surface defining a patient contact area to facilitate thermal energy exchange with the patient, the patient contact area is convertible from a first patient contact area to a second patient contact area, and the second patient contact area is different from the first patient contact area;

expanding the first thermal pad along a single dimension to convert the first patient contact area to the second patient contact area;

applying the first thermal pad to the patient; and delivering the TTM fluid from the TTM module to the first thermal pad.

20. The method of claim 19, further comprising stretching a material of the thermal pad to convert the first patient contact area to the second patient contact area.

21. The method of claim 19, further comprising coupling a second thermal pad to the first thermal pad, the first thermal pad defining the first patient contact area, so that the first patient contact area is combined with a separate second patient contact area of the second thermal pad to define the second patient contact area, wherein the first thermal pad includes a valve that is opened upon coupling the second thermal pad to the first thermal pad.

22. The method of claim 19, further comprising separating a removable portion of the thermal pad from a remaining portion of the thermal pad to convert the first patient contact area to the second patient contact area, the removable portion including a portion of the patient contact surface.

* * * * *